(12) United States Patent
German et al.

(10) Patent No.: US 6,436,667 B1
(45) Date of Patent: Aug. 20, 2002

(54) HUMAN NKX-6.1 POLYPEPTIDE-ENCODING NUCLEOTIDE SEQUENCES

(75) Inventors: Michael S. German, San Francisco, CA (US); M. Alan Permutt, St. Louis, MO (US); Hiroshi Inoue, Yamaguchi (JP)

(73) Assignees: The Regents of the University of California, Oakland, CA (US); Washington University, St. Louis, MO (US)

(*) Notice: Subject to any disclaimer, the term of this patent is extended or adjusted under 35 U.S.C. 154(b) by 0 days.

(21) Appl. No.: 09/009,816

(22) Filed: Jan. 20, 1998

Related U.S. Application Data

(63) Continuation-in-part of application No. 08/900,510, filed on Jul. 25, 1997, now Pat. No. 6,127,598.

(51) Int. Cl.[7] .......................... C07H 21/04; C12P 21/06
(52) U.S. Cl. ................. 435/69.1; 435/325; 435/252.33; 435/320.1; 536/23.5; 536/24.31; 530/350
(58) Field of Search ................................. 530/358, 350; 435/69.1, 320.1, 325, 252.33; 536/23.1, 23.5, 24.31

(56) References Cited

PUBLICATIONS

Rudnick, A. et al., GenBank Database, Accession No. X81409, Sep. 1994.*
Amann, E. et al., Gene, vol. 69, p. 301–315, 1988.*
Jorgensen, M. et al., GenBank, Accession No. AF004431, Jun. 25, 1997.*
Inoue, et al., "Isolation, Characterization, and Chromosomal Mapping of the Human Nkx6.1 Gene (NKX6A), a New Pancreatic Islet Homeobox Gene," *Genomics*, 40: 367–370 (1997).
Nakagawa, et al., "Roles of Cell–Autonomous Mechanisms for Differential Expression of Region–Specific Transcription Factors in Neuroepithelial Cells," *Development*, 122:2449–2464 (1996).
Price, et al., "Regional Expression of the Homeobox Gene Nkx–2.2 in the Developing Mammalian Forebrain," *Neuron*, 8: 241–255 (Feb. 1992).
Rubenstein, et al., "The Embyonic Vertabrate Forebrain: The Prosomeric Model," *Science*, 266: 578–580 (Oct. 28, 1994).
Rudnick, et al., "Pancreatic Beta Cells Express a Diverse Set of Homeobox Genes," *Proc. Natl. Acad. Sci.*, 91: 12203–12207 (Dec. 1994).
Sander and German, "The β Cell Transcription Factors and Development of the Pancreas," *Journal of Molecular Medicine*, 75: 327–340 (1997).
Hartigan, et al., "The cDNA Sequence of Murine Nkx–2.2," *Gene* 168:271–272 (Feb. 12, 1996).
Kim, et al., "Drosophila NK–homeobox Henes," *Proc Natl Acad Sci U S A*. 86:7716–7720 (Oct. 1, 1989).
Shimamura, et al., "Longitudinal Organization of the Anterior Neural Plate and Neural Tube," *Development*, 121:3923–3933 (Dec. 1, 1995).
Barth, et al., "Expression of Zebrafish nk2.2 is Influenced by Sonic Hedgehog/vertebrate Hedgehog–1 and Demarcates a Zone of Neuronal Differentiation in the Embryonic Forebrain," *Development*, 121:1755–1768 (Jun. 1, 1995).
Sussel, et al., "The Nkx–2.2 Homeobox Gene Plays a Critical Role in Islet Cell Development," *Exp. Clin. Endocrinol. Diabetes* 105(4):A20–A21 (1997).

* cited by examiner

*Primary Examiner*—Nashaat T. Nashed
(74) *Attorney, Agent, or Firm*—Bozicevic, Field & Francis LLP; Carol L. Francis; David D. Phinney

(57) ABSTRACT

The present invention features a human Nkx-6.1 polypeptide and nucleotide sequences encoding Nkx-6.1 polypeptides. In a particular aspect, the polynucleotide is the nucleotide sequence of SEQ ID NO:1. In addition, the invention features polynucleotide sequences that hybridize under stringent conditions to SEQ ID NO:1. In related aspects the invention features expression vectors and host cells comprising polynucleotides that encode a human Nkx-6.1 polypeptide. The present invention also relates to antibodies that bind specifically to a human Nkx-6.1 polypeptide, and methods for producing human Nkx-6.1 polypeptides.

8 Claims, 6 Drawing Sheets

FIG. 1A

5' untranslated sequence (SEQ ID NO:9)
cctcgctgcaaggctacggtctccggcgtggcgtgggATGTTAGGCGTGGCCATGGAGCGGCACCGGCAGAGCAT

```
    F   L   L   S   S   P   P   L   A   A   L   H   S   M   A   E   M   K   T   P   L   Y   P   P   A   A   Y   P    41
    TCCTGCTCAGCAGCCCCTCCCCTGGCGGCGCTGCACAGCATGGCTGAGATGAAGACACCCCTGTACCCTCCGGCGTATCCC

P   L   P   A   G   P   P   S   S   S   S   S   S   S   S   S   P   S   P   P   L   G   T   H   N                68
    CGCTGCCTGGCCGGGCCCCCCTCCTCGTCCTCGTCGTCGTCGTCCTCGCCGCCGCCTCTCGGCACCCACAACC

P   G   G   L   K   P   P   A   T   G   G   L   S   S   L   G   S   P   P   Q   Q   L   S   A   A  [T   P]        95
    CAGGGCGGCCTGAAGCCCCCAGCCACGGGGGGCCTCATCCAGCCTGGGCAGCCCCCCAGCAGCTTCTGAGTGCCGCCACCCCAC

H   G   I   N   D   I   L   S   R   P   S   M   P   V   A   S   G   A   A   L   P   S   A   S   P   S   G        122
    ACGGCATCAACGATATCCTGAGCCGGCCCTCCATGCCGGTGGCCTCGGGCGCGGCCCTGCCCTCGGCCTCGCCTTCCGGTT

S   S   S   S   S   S   S   A   S   A   S   S   A   S   S   A   S   A   A   A   A   A   A   A   A   A   A        149
    CCTCCTCGTCCTCCTCCTCGTCGGCCTCGGCCTCCTCGGCCTCTGCCGCCGCCGCCGCCGCCGCCGCCG

A   S   S   P   A   G   L   L   A   G   L   P   R   F   S   S   L   S   P   P   P   P   P   P   G   L   Y        176
    CCTCATCCGCCCGGGACTGCTCGCCGGACTGCCCAGGTTCAGCAGCCTTAGCCCCCCGCCCCCCGGCTCTACT

F   S   P   S   A   A   A   V   A   A   V   G   R   Y   P   K   P   L   A   E   L   P   G   R   T   P   I        203
    TTCAGCCCCAGCGCGGCGGCGGTGGCAGCCGTACCCCAAGCCGCTGGCTGAGCTGCCTGGCCGGACCCCCATCT

F   W   P   G   V   M   Q   S   P   P   W   R   D   A   R   L   A   C   T   P (SEQ ID NO:4)                        223
    TCTGGCCCGGAGTGATGCAGAGCCCGCCTTGGAGGACGCCAGGCTTGCCTGCACCCCCTgtgagtactaccacccgcgcc
                                                                    (SEQ ID NO:3)▲
``` ccga....(SEQ ID NO:10)    (intron 1: 1.5 kb)

Exon I

FIG. 1B

```
                                                                       H  Q  G  226
...tcgttgttattggtttctcacacaATCAAGGA
                                                     (SEQ ID NO:11)▲
       S  I  L  L  D  K  D  G  K  R  K  H  T  R  P  T  F  S  G  Q  Q  I  F  A  L  E  K  253
       TCCATTTTGTTGGACAAAGATGGGAAGAGGAAGCACACGAGACCCACTTTTTCGGACCAGATCTTCGCCCTGGAGAAG
Exon II
       T  F  E  Q  T  K  Y  L  A  G  P  E  R  A  R  L  A  Y  S  L  G  M  T  E  S  Q  V  280
       ACTTTCGAACAAACAAAATACTTGGCGGGACCCGAGAGGGCCCGTCTGGCCTATTCGTTGGGAATGACAGAGAGTCAGGTC
       K (SEQ ID NO:6)                                                                 281
       AAgtgagtgagtggacctgcatacctggag...(SEQ ID NO:12) (intron 2: 2.1 kb)...tctcctccttttctccg
(SEQ ID NO:5)▲
       V  W  F  Q  N  R  R  T  K  W  R  K  K  H  A  A  E  M  A  T  A  K  K  K  Q  306
       cctcagGTCTGGTTCCAGAACCGGCGGACCAAGTGGAGGAAGAAGCACGCTGCGGAGATGGCCACGGCCAAGAAGAAGCAG
(SEQ ID NO:13)▲
       D  S  E  T  E  R  L  K  G  A  S  E  N  E  E  E  D  D  D  Y  N  K  P  L  D  P  N  333
       GACTCGGAGACAGAGAGGCTCAAGGGCGCTTCAGAGAATGAGGAGGAGGACGACGACTACAATAAGCCTCTGGATCCCAAC
Exon III
       S  D  D  E  K  I  T  Q  L  L  K  K  H  K  S  S  G  G  G  G  G  L  L  L  H  A  360
       TCGGACGACGAGAAAATCACGCAGCTGTTGAAGAAGCACAAGTCCAGCGGGGGCGGCGGCCTCCTACTGCAGGCG
       S  E  P  E  S  S  S  stop (SEQ ID NO:8)                                         367
       TCCGAGCCCGAGAGCTCATCCTGAacgccgccgccgccgccacctttccggctccggctccacctctgggcggggaggg
                                                                        (SEQ ID NO:7)
                       3' untranslated sequence
                       (SEQ ID NO:14)
```

```
HumanNkx6.1Promoter(1)   ------------- ------------- ------------- ------------- --GAATTCTC    8
Mouse Nkx6.1 Promoter(1) TGTGACACTC CCCCCCCCCC CCCACTGGTG TATCAACTGC CCGATTTCTC 1800

HumanNkx6.1Promoter(1)   AAAATTGTCA AGGGTTTTC  CTTCTCCAGC CCGCAGTTCA ACCCTGTCGG   58
Mouse Nkx6.1 Promoter(1) AAGATCGACC AAAGAGGTTT TTTCCTTGGT T--TTGGTCA ACCCGAGCA  1848

HumanNkx6.1Promoter(1)   GAACGTAAAG ATCAGCCAGA GATGGAAGAG ATTTAGAGAG TAAAG-----  103
Mouse Nkx6.1 Promoter(1) GACCTTAAAG ATCGGCCAGA GGGAGCAAAG CCCTTTTGAC CATCGCTCCC 1898

HumanNkx6.1Promoter(1)   GAAGCCACCC TTCAACTC-- ----CTAAAC TCTAGATAGA CATCCC----  143
Mouse Nkx6.1 Promoter(1) AATGCCAGCC TAGAAGTCGG TCGTCTCTAG TTTACTCAAC TACCCCGAGT 1948

HumanNkx6.1Promoter(1)   ---ACC---- ACCA--CTGT CCAGGAGCT- ---------- ----GGTAC   168
Mouse Nkx6.1 Promoter(1) TGAGAGCTTG ACCAGGCTTT CCAACAGTTA CCTGTCTTCC CCGAGGTAT  1998

HumanNkx6.1Promoter(1)   ATCTCCATCT CCCGTAGC-- ----AACTCT AG-AATTGGG ---------AGT  204
Mouse Nkx6.1 Promoter(1) TCCTCTATCT AAAGTTGCCC TGTGAATTTT AGTGATCCTG CCTCATAAAT 2048

HumanNkx6.1Promoter(1)   AGGCGCCAGA GTTTTGGA-- GAGGGTTTTC AAAAGCTTAC AGTTCCCAGG   252
Mouse Nkx6.1 Promoter(1) CCAACCAATA ATATAGAGG  GAGGATTTTA AAAA------ ----------  2082

HumanNkx6.1Promoter(1)   GTGTACCTAG ATGCTTCTGT ATCTAAAGTT TCCGCCTGAA TTTTGATGAT   302
Mouse Nkx6.1 Promoter(1) ---------- ---------- ---------- ---------- ----------  2082

HumanNkx6.1Promoter(1)   TCTACCCCCA TGTAAACCCA AAGGAAATAA CAACAATAAT CAAAGGGAGA   352
Mouse Nkx6.1 Promoter(1) ---------- ---------- ---------- ----ATAAT  TA--------  2089

HumanNkx6.1Promoter(1)   AAAGTTAAGG GAAAAAACTC CCTCACTGTT CTCAGGTATA AACATCATCT   402
Mouse Nkx6.1 Promoter(1) ---------- ---------- TCTCATTTCT GTTAGGTTTA GACACCAGC  2119

HumanNkx6.1Promoter(1)   GACAGATAAA TATTCCTATT AAACGGATTC AGTTTCAGC  GAATTGAGTA   452
Mouse Nkx6.1 Promoter(1) AGGAGATAAA TATTCTCATT AAGCTGATTT CATCCCCAGA GTACTGAGCC 2169

HumanNkx6.1Promoter(1)   ACC-CATAAA TGATAATGAA CGGGTGGA  AGCGACGGGC GGGGGGAAC    501
Mouse Nkx6.1 Promoter(1) CCCTCATAAG TGATAATGAT C----TAGGG AGT------- ----GGGA-- 2202

HumanNkx6.1Promoter(1)   TCGGGAATGA AAAAAAAAAT AAAGTGGAGG AGAAAGAACA GAAAAGGAAA   551
Mouse Nkx6.1 Promoter(1) ---GAGCGA  AGACAAGAAC -------GG AGAAAGAACA GAAAAG---A 2237

HumanNkx6.1Promoter(1)   GCAGGAGGTG GAAAGATGGA AGAGGACGAT CCTTTGGCCT ACAAGGGGAT   601
Mouse Nkx6.1 Promoter(1) GCAGGAGACA GAAAGATGGT GAAGGGTGAC CCTTAGGCCT GCGAGGGGAT 2287

HumanNkx6.1Promoter(1)   TAAGGACATC TATAAGGCTT AAGGAGCAAC AAATTAATTT ACACAATTCT   651
Mouse Nkx6.1 Promoter(1) TTAAAAACAT CTACGGGCTT AAGGAACAAC AAATCAATTT ACACGGTTCT 2337
```

FIG. 4B

```
HumanNkx6.1Promoter(1)    GGGAGAGCCC AGATGCCTT TAATTAATCC CTTCAAAAGA AGGAGCCAGG  701
Mouse Nkx6.1 Promoter(1)  GGAAGAGCCC AGAGGGCCTT TAATTAATCC CTTCAAAAGA AGGAAGTCGG  2387

HumanNkx6.1Promoter(1)    CCAGGGCTGC GCCGGCTGCC TGCTCCATTA GCTCCATTT -ACAAGGGAC  750
Mouse Nkx6.1 Promoter(1)  CCTGGGATGT GCCTTCCTGCC TGCTCCATTA GCTCCCTTTT CGCAAGGGTC  2437

HumanNkx6.1Promoter(1)    CAGACTTGGT TCGAGGTGAG GCGCCCTCCA GAGCTGGTGG GGGAAGGGGA  800
Mouse Nkx6.1 Promoter(1)  CAGACACCGT TGGAGGTGGG CGCTGCCGC AAGCTGGTGG GGG------  2480

HumanNkx6.1Promoter(1)    TAGGATGACG CGAGCGGGCT AGTGGGAAG CAAGGAAGA ATATGAACTG  850
Mouse Nkx6.1 Promoter(1)  -AGGATGACG CGAGCTGGC- -GTGGG--CG GAAGAGACGC ACTTAAACTG  2525

HumanNkx6.1Promoter(1)    CTTTTCCATA AAAGGGCTGA GTTTTCATTA TTCCTCTCTT TAAAAAGTAA  900
Mouse Nkx6.1 Promoter(1)  CTTTTCCATA GAAGGGCTGG ATTTTCATTA TTCCTCTCTT TAAAAAGTAA  2575

HumanNkx6.1Promoter(1)    TACCCTCTTC GTCTCTGCTT CCCCCTCCCC TTTTCTCATTT TATTTAGCAC  950
Mouse Nkx6.1 Promoter(1)  TGCCCTCTTC GTCCGTGCTC CCTCCTTCTC CTTTCCATTT TATTTTGCAC  2625

HumanNkx6.1Promoter(1)    AATTAATTGA GGCGGCCACT GGCCCCAGCG CGGAACCGCA CCACTCACCA  1000
Mouse Nkx6.1 Promoter(1)  AATTAGTTGA GCCGGCCGCT GGCTCTAGAC TGGAACCACT CTTTTCGCCA  2675

HumanNkx6.1Promoter(1)    GCTCCCGCCC CTCCTGGCCC CGCCCACACG CCCTACGCCT AGGGAGCGGG  1050
Mouse Nkx6.1 Promoter(1)  GGCCCCTCCC CTCTTGGCTC CGCCCA---- --AGTGAAGC TG-----GGG  2714

HumanNkx6.1Promoter(1)    AGGGGACTAG GCGGGGCGCG CCCTACGCCT GGCCCGCCTC AGCCAATCAG  1100
Mouse Nkx6.1 Promoter(1)  CGGGGACTAG GAGGGCGCGT CCCTTATGCT CCCTAGTCTC AGCAATCAA   2764

HumanNkx6.1Promoter(1)    AGGGTGCGGC GCCCCGAGT GGGCGAGCC CAGGGGCGAC GCAAGGATCG  1150
Mouse Nkx6.1 Promoter(1)  AAGCTGTGGC GCTCCCAGTT AGGCGTGTTC TAGGAGCGAC GCCTTG-CCC  2813

HumanNkx6.1Promoter(1)    AGGCGGGCGAG CTATTGGACA CGGTGGTTAC GCCCCCGGCC TGCGCCCGGC  1200
Mouse Nkx6.1 Promoter(1)  AAGCTGAGCG CTATTGGAGG CGGTGTTTAC GCCC-AGGAC -----------  2852

HumanNkx6.1Promoter(1)    TCGCCCGGCCC CCGC------ -------- ------AGC CTCGGAGTGA  1227
Mouse Nkx6.1 Promoter(1)  ---CCGGGCC CCGCTCCTCA GTCCCGCCCC GCCGAGCCGC CCCGGAATGA  2899

HumanNkx6.1Promoter(1)    CGTCCCTCAA AGTTCTCATT TTGGTCCCCC ACTTCCCCCT CCCTTTCGTC  1277
Mouse Nkx6.1 Promoter(1)  CGTCCTCGAA AGTTCTCATT TTGGCCCCCC ACCT-CCCCT CCCTTGCGTC  2948

HumanNkx6.1Promoter(1)    CCCCAGCTAA AGAGGGGTAG GGAGTGATGC AAATGTTTTA TT(SEQ ID NO:20)1319
Mouse Nkx6.1 Promoter(1)  CCCCAGCTAA AGAGAGGCAG GGAGGGGTGC AAATATTTTA TT(SEQ ID NO:21)1990
```

HUMAN NKX-6.1 POLYPEPTIDE-ENCODING NUCLEOTIDE SEQUENCES

CROSS-REFERENCE TO RELATED APPLICATIONS

This application is a continuation-in-part of U.S. application Ser. No. 08/900,510, filed Jul. 25, 1997, now U.S. Pat. No. 6,127,598 which application is incorporated herein by reference.

STATEMENT AS TO FEDERALLY SPONSORED RESEARCH

This invention was made, at least in part, with government grants from the National Institutes of Health (Grant Nos. DK41822, DK16746, DK41822, and HG01066). Thus, the U.S. government may have certain rights in this invention.

FIELD OF THE INVENTION

The invention relates generally to the field of nucleotide sequences encoding gene products having a role in pancreatic development, neural development, diabetes, depression, and/or obesity.

BACKGROUND OF THE INVENTION

Diabetes mellitus is the third leading cause of death in the U.S. and the leading cause of blindness, renal failure, and amputation. Diabetes is also a major cause of premature heart attacks and stroke and accounts for 15% of U.S. health care costs. Approximately 5% of Americans, and as many as 20% of those over the age of 65, have diabetes.

Diabetes results from the failure of the β-cells in the islets of Langerhans in the endocrine pancreas to produce adequate insulin to meet metabolic needs. Diabetes is categorized into two clinical forms: Type 1 diabetes (or insulin-dependent diabetes) and Type 2 diabetes (or non-insulin-dependent diabetes). Type 1 diabetes is caused by the loss of the insulin-producing β-cells. Type 2 diabetes is a more strongly genetic disease than Type 1 (Zonana & Rimoin, 1976 N. Engl. J. Med. 295:603), usually has its onset alter in life, and accounts for approximately 90% of diabetes in the U.S. Affected individuals usually have both a decrease in the capacity of the pancreas to produce insulin and a defect in the ability to utilize the insulin (insulin resistance). Obesity causes insulin resistance, and approximately 80% of individuals with Type 2 diabetes are clinically obese (greater than 20% above ideal body weight). Unfortunately, about one-half of the people in the U.S. affected by Type 2 diabetes are unaware that they have the disease. Clinical symptoms associated with Type 2 diabetes may not become obvious until late in the disease, and the early signs are often misdiagnosed, causing a delay in treatment and. increased complications. While the role of genetics in the etiology of type 2 diabetes is clear, the precise genes involved are largely unknown.

Depression and obesity can each be associated with a defect in serotonin production, serotonin metabolism, or serotonin-mediated neurotransmission. Serotonin (5-hydroxytryptamine (5HT)) is a biogenic amine that not only functions as a neurotransmitter (Takaki, et al., 1985 J. Neurosciences 5:1769) and as a hormone, (Kravitz, et al., 1980 J. Exp. Biol. 89:159), but also as a mitogen (Nemeck, et al., 1986 Proc. Natl. Acad. Sci. USA 83:674). In its functions as a neurotransmitter, serotonin modulates many forms of synaptic transmission and is believed to exert a number of effects on neuronal growth during early development. In addition, serotonin is also believed to modulate numerous sensory, motor, and behavioral processes in the mammalian nervous system (see Jacobs. in Hallucinogens: Neurochemical, Behavior, and Clinical Perspectives (eds. Jacobs) 183–202 (Raven, N.Y., 1984), Sleight et al., in Serotonin Receptor Subtypes: Basic and clinical aspects. (eds. Peroutka) 211–227 (Wiley-Liss, New York, N.Y., 1991. Wilkinson et al. in Serotonin receptor subtypes: Basic and clinical aspects (eds. Peroutka) 147–210 (Wily-Liss, New York, N.Y. 1991)). In the cortex, transmission at serotoneurgic synapses contributes to affective and perceptual states; these synapses represent a major site of action of psychotropic drugs such as LSD, Jacobs in Hallucinogens: Neurochemical, Behavioral, and Clinical Perspectives, Jacobs, Ed. (Raven Press, New York, 1984), pages. 183–202.

The diverse responses elicited by serotonin are mediated through the activation of a large family of receptor subtypes, Tecott et al. 1993 Curr. Opin. Neurobiol 3:310–315. The complexity of this signaling system and the paucity of selective drugs have made it difficult to understand development of serotonin-producing cells and to understand the role of serotonin in depression and obesity.

Attempts to understand depression and other serotonin-related disorders have focused upon understanding the development of the brain. Development of the vertebrate forebrain is an elaborate process that gives rise to a variety of essential structures including the cerebral cortex, basal ganglia, hypothalamus and thalamus. Although much is known about these structures and the functions that they perform, very little is understood about the mechanisms that direct their specification, morphogenesis and differentiation. Recently, however, families of candidate regulatory genes with regionally restricted expression in the neuroepithelium of the forebrain have been identified; these gene families are hypothesized to establish positional identity and to control region-specific morphogenesis and histogenesis of the forebrain (Shimamura et al. 1995 Development, 121:3923–3933; Rubenstein, et al., 1994 Science 266:578–581).

Nkx-2.1 and Nkx-2.2 are two of the earliest known genes to be expressed in the neuroectodermal cells of the forebrain; they are expressed at the onset of neurulation in restricted ventral forebrain domains (Shimamura et al., 1995 supra). In addition, expression of these genes is induced by the secreted molecule sonic hedgehog (Shh), a known axial mesendodermal signaling protein that is responsible for the induction of the ventral neurons of the forebrain (Ericson et al., 1995 Cell 81:747–756; Barth and Wilson, 1995, Development 121:1755–1768). The early and spatially limited expression of Nkx-2.1 and Nkx-2.2 in response to a primary inductive signal suggests that these molecules provide the initial positional information for specific ventral regions of the developing forebrain.

Nkx-2.2 is a member of a vertebrate gene family that is homologous to the Drosophila NK-2 gene, which is expressed in neuroblast precursors in the Drosophila head (Kim and Nirenberg, 1989 Proc. Natl. Acad. Sci. USA. 86:7716–7720). The NK-2 gene family is characterized by two regions of homology: the homeobox and a highly conserved sequence downstream of the homeobox.

In addition to its expression in the brain, Nkx-2.2 is also expressed in the pancreas, pancreatic islet β cells, and hamster insulinoma (HIT) cells (Rudnick et al. 1994 Proc. Natl. Acad. Sci. USA 91:12203–12207). Nkx-2.2 expression in pancreas is accompanied by expression of Nkx-6.1, another NK-2-related gene (Rudnick et al. supra). A partial sequence (Price et al. 1992 Neuron 8:241–255) and a full-length sequence of murine Nkx-2.2 (Hartigan and Rubenstein 1996 Gene 168:271–2) have been published. The actual function of Nkx-2.2 or Nkx-6.1 as either transcription factors or as developmental regulators was not previously known.

The pathogenesis of diabetes, depression, and obesity, and the links between these diseases, are complex and not well understood. Moreover, the complex nature of these disorders makes their study difficult. Thus, there is a need for an in vivo model for insulin- and serotonin-producing cells for identification of new compounds for treatment of disorders associated with insulin and serotonin production, as well as for development of new therapies to address such disorders (e.g., methods for replacing or enhancing serotonin-producing and/or insulin-producing cells). In addition, there is a need for a method to identify individuals at risk of developing insulin and serotonin production-associated disorders. Finally, there is little known about the development and differentiation of the pancreatic islet cells or key cell types in the central nervous system.

SUMMARY OF THE INVENTION

The present invention features a human Nkx-6.1 polypeptide and nucleotide sequences encoding a human Nkx-6.1 polypeptide. In a particular aspect, the polynucleotide is the nucleotide sequence of SEQ ID NO:1. In addition, the invention features polynucleotide sequences that hybridize under stringent conditions to SEQ ID NO:1. In related aspects the invention features expression vectors and host cells comprising polynucleotides that encode a human Nkx-6.1 polypeptide. The present invention also relates to antibodies that bind specifically to a human Nkx-6.1 polypeptide, and methods for producing human Nkx-6.1 polypeptides.

In one aspect the invention features a method for identifying compounds that bind a human Nkx-6.1 polypeptide.

Yet another aspect of the invention relates to use of human Nkx-6.1 polypeptides and specific antibodies thereto for the diagnosis and treatment of human disease.

A primary object of the invention is to provide an isolated human Nkx-6.1 polypeptide-encoding polynucleotide for use in expression of human Nkx-6.1 (e.g, in a recombinant host cell) and for use in, for example, identification of human Nkx-6.1 polypeptide binding compounds (especially those compounds that affect human Nkx-6.1 polypeptide-mediated activity)

Another object of the invention is to provide an isolated human Nkx-6.1 polypeptide-encoding polynucleotide for use in generation of non-human transgenic animal models for Nkx-6.1 gene function, wherein the transgenic animal is characterized by having a defect in Nkx-6.1 gene function, and by having a decreased number of insulin-producing cells relative to a normal animal of the same species. Such Nkx-6.1 transgenic animals are further characterized by a decreased number of serotonin-producing cells relative to a normal animal of the same species. Another related object of the invention is to provide non-human transgenic mammals that are characterized by excess or ectopic expression of the Nkx-6.1 gene.

These and other objects, advantages and features of the present invention will become apparent to those persons skilled in the art upon reading the details of the invention more fully set forth below.

The invention will now be described in further detail.

BRIEF DESCRIPTION OF THE FIGURES

FIGS. 1A and 1B shows the genomic sequence of human Nkx-6.1 polypeptide.

Figure 3:
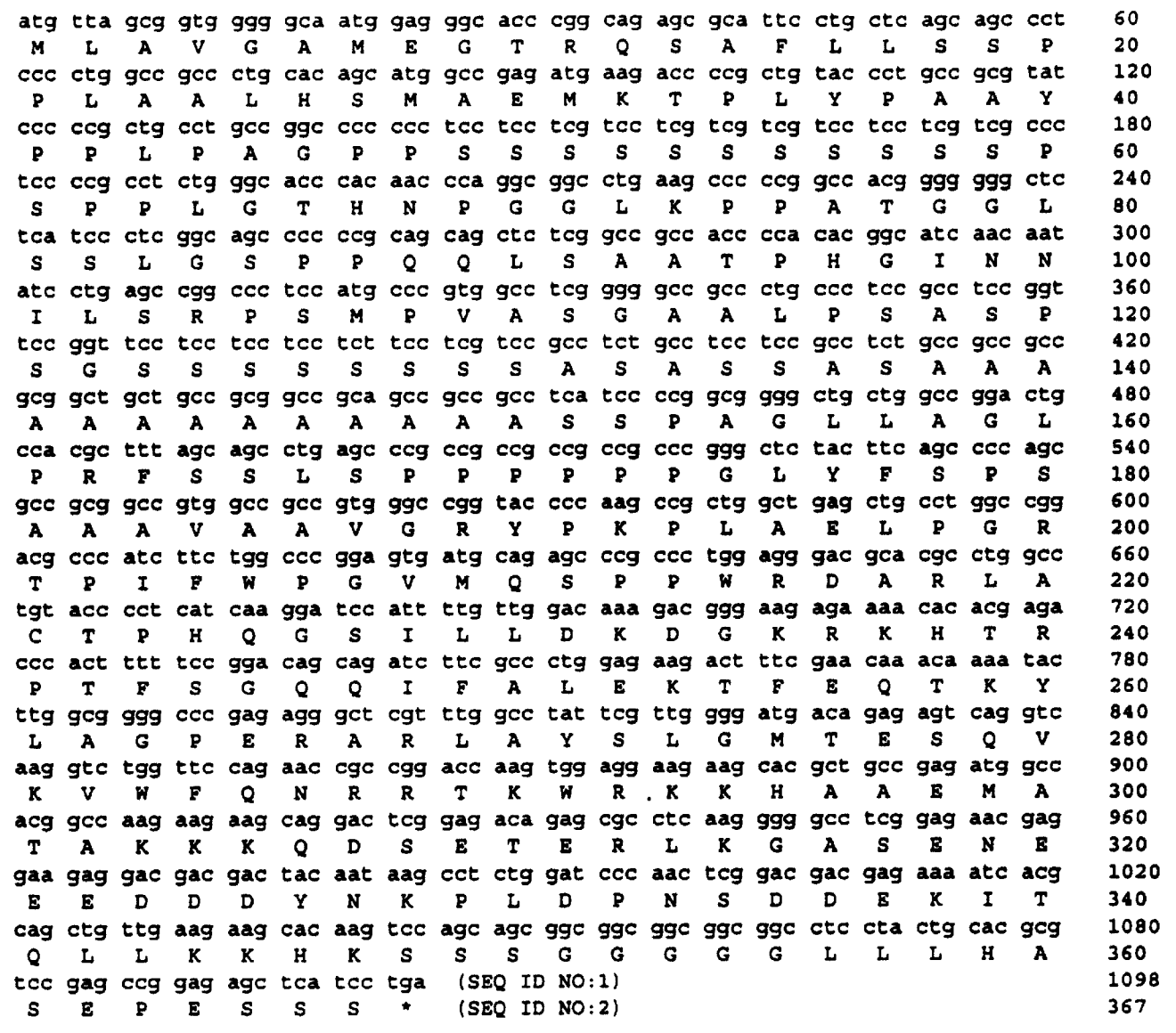

FIG. 3 shows the relationship between the hNkx-6.1 nucleotide coding sequence (SEQ ID NO:1) and the hNkx-6.1 polypeptide amino acid sequence (SEQ ID NO:2).

FIGS. 4A and 4B is an alignment of the mouse human Nkx-6.1 promoter sequence and the human Nkx-6.1 promoter sequence.

DETAILED DESCRIPTION OF THE INVENTION

Figure 2:
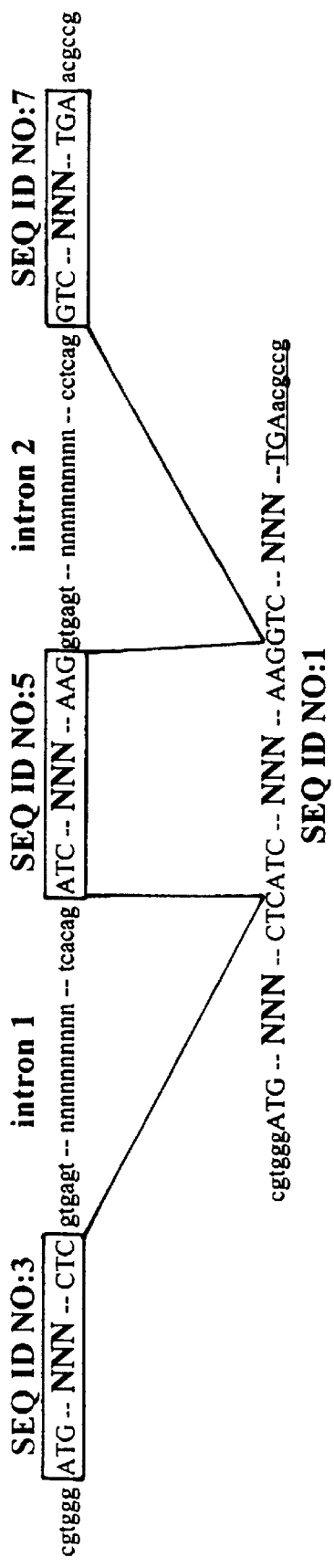
FIG. 2 illustrates the splicing junctions of the sequence encoding the human Nkx-6.1 polypeptide. Uppercase letters represent coding region, while lowercase letters represent either untranslated or intronic sequences. The letter n represents intervening sequence, and is different for each represented segment.

Before the present nucleotide and polypeptide sequences are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated-herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or anti-sense strand. Where "polynucleotide" is used to refer to a specific polynucleotide sequence (e.g. an Nkx-6.1 polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule.

By "antisense polynucleotide" is mean a polynucleotide having a nucleotide sequence complementary to a given polynucleotide sequence including polynucleotide sequences associated with the transcription or translation of the given polynucleotide sequence (e.g, a promoter), where the antisense polynucleotide is capable of hybridizing to a polynucleotide sequence. Of particular interest are antisense-polynucleotides capable of inhibiting transcription and/or translation, either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al 1993 Anticancer Drug Des 8:53–63).

As used herein, "Nkx-6.1 polypeptide" refers to the amino acid sequences of an isolated Nkx-6.1 polypeptide obtained from any species, particularly mammalian, including human, rodenti (e.g., murine or rat), bovine, ovine, porcine, murine, or equine, preferably rat or human, from any source whether natural, synthetic, semi-synthetic or recombinant. "Human Nkx-6.1 polypeptide" refers to the amino acid sequences of isolated human Nkx-6.1 polypeptide obtained from a human, and is meant to include all naturally-occurring allelic variants, and is not meant to limit the amino acid sequence to the complete, native amino acid sequence associated with the recited protein molecule.

The term "biologically active" refers to human Nkx-6.1 polypeptide having structural, regulatory, or biochemical functions of a naturally occurring polypeptide. Likewise, "immunologically active" defines the capability of the natural, recombinant or synthetic human Nkx-6.1 polypeptide, or any oligopeptide thereof, to induce a specific immune response in appropriate animals or cells and to bind with specific antibodies.

The term "derivative" as used herein refers to the chemical modification of a nucleic acid encoding a human Nkx-6.1 polypeptide or the encoded human Nkx-6.1 polypeptide. Illustrative of such modifications would be replacement of hydrogen by an alkyl, acyl, or amino group. A nucleic acid derivative would encode a polypeptide which retains essential biological characteristics of a natural polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs 1994 Dictionary of Biotechnology, Stockton Press, New York N.Y.). Amplification as carried out in the polymerase chain reaction technologies is described in Dieffenbach et al. 1995, PCR Primer, a Laboratory Manual, Cold Spring Harbor Press, Plainview N.Y.

By "transformation" is meant a permanent or transient genetic change, preferably a permanent genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

By "construct" is meant a recombinant nucleic acid, generally recombinant DNA, that has been generated for the purpose of the expression of a specific nucleotide sequence (s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by an Nkx-6.1 sequence).

By "Nkx-6.1 associated disorder" is meant a physiological condition or disease associated with altered Nkx-6.1 function (e.g., due to aberrant Nkx-6.1 expression or a defect in Nkx-6.1 expression or in the Nkx-6.1 protein). Such Nkx-6.1 associated disorders can include, but are not necessarily limited to, disorders associated with reduced levels of insulin or the ability to utilize insulin (e.g., hyperglycemia, diabetes (e.g., Type 1 and Type 2 diabetes, and the like), Parkinson's, disorders associated with reduced serotonin production (e.g,. depression and obesity), and disorders associated with neural defects (e.g., defects in motor neurons, serotonin-producing neurons, dopamine neurons, and developmental defects in the forebrain, midbrain, hindbrain, and spinal cord).

By "Nkx-6.1 associated disorder" is meant a physiological condition or disease associated with altered Nkx-6.1 function (e.g., due to aberrant Nkx-6.1 expression or a defect in Nkx-6.1 expression or in the Nkx-6.1 protein). Such Nkx-6.1 associated disorders can include, but are not necessarily limited to, disorders associated with reduced levels of insulin or the ability to utilize insulin (e.g., hyperglycemia, diabetes (e.g., Type 1 and Type 2 diabetes, and the like), Parkinson's, and disorders associated with neural defects (e.g., defects in motor neurons, serotonin-producing neurons, dopamine neurons, and developmental defects in the forebrain, midbrain, hindbrain, and spinal cord).

By "subject" or "patient" is meant any subject for which therapy is desired, including humans, cattle, dogs, cats, guinea pigs, rabbits, rats, mice, insects, horses, chickens, and so on. Of particular interest are subjects having an Nkx-6.1-associated disorder which is amenable to treatment (e.g., to mitigate symptoms associated with the disorder) by expression of either Nkx-6.1-encoding nucleic acid in a cell of the subject (e.g., by introduction of the Nkx-6.1-encoding nucleic acid into the subject in vivo, or by implanting Nkx-6.1-expressing cells into the subject, which cells also produce a hormone that the subject is in need of (e.g., insulin or serotonin)).

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammnal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. A knock-out of an Nkx-6.1 gene means that function of the Nkx-6.1 gene has been substantially decreased so that Nkx-6.1 expression is not detectable or only present at insignificant levels. "Knock-out" transgenics of the invention can be transgenic animals having a heterozygous knock-out of the Nkx-6.1 gene, a homozygous knock-out of the Nkx-6.1 gene, or any combination thereof. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. "Knock-in" transgenics of the invention can be transgenic animals having a heterozygous knock-in of the Nkx-6.1 gene or a homozygous knock-in of the Nkx-6.1 gene. "Knock-ins" also encompass conditional knock-ins.

Overview of the Invention

The present invention is based upon the identification and isolation of a polynucleotide sequence encoding a human Nkx-6.1 polypeptide. Accordingly, the present invention encompasses such human Nkx-6.1 polypeptide-encoding polynucleotides, as well as human Nkx-6.1 polypeptides encoded by such polynucleotides. Expression of Nkx-6.1 is linked to both pancreatic and neural development. Specifically, Nkx-6.1 expression is necessary for development of β cells, the cells responsible for insulin production that are located in the islets of Langerhans in the pancreas. Furthermore, Nkx-6.1 expression is also essential for development of serotonin-secreting cells in the brain.

The invention also encompasses the use of the polynucleotides disclosed herein to facilitate identification and isolation of polynucleotide and polypeptide sequences having homology to a human Nkx-6.1 polypeptide of the invention. The human Nkx-6.1 polypeptides and polynucleotides of the invention are also useful in the identification of human Nkx-6.1 polypeptide-binding compounds, particularly human Nkx-6.1 polypeptide-binding compounds having human Nkx-6.1 polypeptide agonist or antagonist activity. In addition, the human Nkx-6.1 polypeptides and polynucleotides of-the invention are useful in the diagnosis, prevention and treatment of disease associated with human Nkx-6.1 polypeptide biological activity.

The human Nkx-6.1 polypeptide-encoding polynucleotides of the invention can also be used as a molecular probe with which to determine the structure, location, and expression of the human Nkx-6.1 polypeptide and related polypeptides in mammals (including humans) and to investigate potential associations between disease states or clinical disorders and defects or alterations in human Nkx-6.1 polypeptide structure, expression, or function.

Nkx-6.1 Nucleic Acid

The term "Nkx-6.1 gene" is used generically to designate Nkx-6.1 genes and their alternate forms. "Nkx-6.1 gene" is also intended to mean the open reading frame encoding specific Nkx-6.1 polypeptides, introns, and adjacent 5' and 3' non-coding nucleotide sequences involved in the regulation of expression, up to about 1 kb beyond the coding region, but possibly further in either direction. The DNA sequences encoding Nkx-6.1 may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the Nkx-6.1 polypeptide.

Genomic Nkx-6.1 sequences have non-contiguous open reading frames, where introns interrupt the protein coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where Nkx-6.1 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. 1995 Mol Med 1:194–205; Mortlock et al. 1996 Genome Res. 6: 327–33; and Joulin and Richard-Foy (1995) Eur J Biochem 232: 620–626.

The regulatory sequences may be used to identify cis acting sequences required for transcriptional or translational regulation of Nkx-6.1 expression, especially in different tissues or stages of development, and to identify cis acting sequences and trans acting factors that regulate or mediate Nkx-6.1 expression. Such transcriptional or translational control regions may be operably linked to an Nkx-6.1 gene or other genes in order to promote expression of wild type or altered Nkx-6.1 or other proteins of interest in cultured cells, or in embryonic, fetal or adult tissues, and for gene therapy.

The nucleic acid compositions used in the subject invention may encode all or a part of the Nkx-6.1 polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The Nkx-6.1 gene is isolated and obtained in substantial purity, generally as other than an intact mammalian chromosome. Usually, the DNA will be obtained substantially free of other nucleic acid sequences that do not include an Nkx-6.1. sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying homologs of Nkx-6.1. Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. 1990 J Mol Biol 215:403–10.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, C. elegans, etc.

The Nkx-6.1-encoding DNA may also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, MRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of MRNA hybridizing to an Nkx-6.1 sequence is indicative of Nkx-6.1 gene expression in the sample.

The Nkx-6.1 nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the Nkx-6.1 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of Nkx-6.1 polypeptides with other polypeptides (e.g., Nkx-6.1), or to alter properties of the proteins that affect their function or regulation. Such modified Nkx-6.1 sequences can be used to, for example, generate the transgenic animals.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

Nkx-6.1 Transgenic Animals

The Nkx-6.1-encoding nucleic acids can be used to generate genetically modified non-human animals or site specific gene modifications in cell lines. The term "transgenic" is intended to encompass genetically modified animals having a deletion or other knock-out of Nkx-6.1 gene activity, having an exogenous Nkx-6.1 gene that is stably transmitted in the host cells, "knock-in" having altered Nkx-6.1 gene expression, or having an exogenous Nkx-6.1 promoter operably linked to a reporter gene. Of particular interest are homozygous and heterozygous knock-outs of Nkx-6.1. Transgenics that are homozygous knock-outs for Nkx-6.1 are likely of less interest due to the lethality of this combination. Transgenics that are heterozygous knock-outs for Nkx-6.1 may be susceptible to an Nkx-6.1-associated disorder (e.g,. diabetes, obesity) at a later age.

Transgenic animals may be made through homologous recombination, where the Nkx-6.1 locus is altered. Alternatively, a nucleic acid construct is randomly integrated into the genome. Vectors for stable integration include plasmids, retroviruses and other animal viruses, YACs, and the like. Of interest are transgenic mammals, preferably a mammal from a genus selected from the group consisting of Mus (e.g., mice), Rattus (e.g., rats), Oryctologus (e.g., rabbits) and Mesocricetus (e.g., hamsters). More preferably the animal is a mouse which is defective or contains some other alteration in Nkx-6.1 gene expression or function. Without being held to theory, within the pancreas Nkx-6.1 apparently acts as a transcriptional activator in a cascade pathway upstream of the transcriptional activity of Nkx-6.1. Therefore, alteration of Nkx-6.1 function will affect Nkx-6.1 function (e.g., a Nkx-6.1 knock-out transgenic animal will have no or little Nkx-6.1 activity present in cells normally exhibiting such activity).

A "knock-out" animal is genetically manipulated to substantially reduce, or eliminate endogenous Nkx-6.1 function, preferably such that target gene expression is undetectable or insignificant. Different approaches may be used to achieve the "knock-out". A chromosomal deletion of all or part of the native Nkx-6.1 homolog may be induced. Deletions of the non-coding regions, particularly the promoter region, 3' regulatory sequences, enhancers, or deletions of gene 6.1 genes. A functional knock-out may also be achieved by the introduction of an anti-sense construct that blocks expression of the native Nkx-6.1 gene (for example, see Li and Cohen (1996) Cell 85:319–329).

Homozygous knock-outs of the endogenous Nkx-6.1 gene results in a dramatic decrease in insulin production as well as severe neural defects. Because transgenic animals having a homozygous knock-out of the Nkx-6.1 gene do not survive long after birth (e.g, null Nkx-6.1 mice survive no more than a few days postnatally (e.g., from about 3 days to about 6 days), use of transgenic animals heterozygous for an Nkx-6.1 gene knock-out, or transgenic animals homozygous for a less severe defect in Nkx-6.1 (e.g., a defect that is not lethal within a few hours to days after birth) may be useful as well.

For example, a defect in Nkx-6.1 function is associated with a decrease in glucokinase expression in the pancreas in homozygous Nkx-6.1 knock-outs (see Examples below). Since glucokinase is the rate-limiting step in β cell glucose sensing, even modest reductions in glucokinase expression due to altered Nkx-6.1. expression (e.g., due to a heterozygous defect in Nkx-6.1) could decrease β cell glucose sensitivity and causes inadequate insulin production and secretion. Moreover, homozygous null Nkx-6.1 transgenics had roughly normal islet amyloid polypeptide (amylin) expression (see the Examples below). Since amyloid deposits of this peptide have been proposed to cause β cell damage and progressive loss of insulin production in type 2 diabetes, a decreased ratio of insulin/amylin production in individuals with decreased Nkx-6.1 may be another contributor to the disease.

Conditional knock-outs of Nkx-6.1 gene function can also be generated. Conditional knock-outs are transgenic animals that exhibit a defect in Nkx-6.1 gene function upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of Nkx-6.1 gene function can be produced using the Cre-loxP recombination system (see, e.g., Kilby et al. 1993 Trends Genet 9:413421). Cre is an enzyme that excises the DNA between two recognition sequences, termed loxP. This system can be used in a variety of ways to create conditional knock-outs of Nkx-6.1. For example, two independent transgenic mice can be produced: one transgenic for an Nkx-6.1. sequence flanked by loxP sites and a second transgenic for Cre. The Cre transgene can be under the control of an inducible or developmentally regulated promoter (Gu et al. 1993 Cell 73:1155–1164; Gu et al. 1994 Science 265:103–106), or under control of a tissue-specific or cell type-specific promoter (e.g., a pancreas-specific promoter or brain tissue-specific promoter). The Nkx-6.1 transgenic is then crossed with the Cre transgenic to produce progeny deficient for the Nkx-6.1 gene only in those cells that expressed Cre during development.

Transgenic animals may be made having an exogenous Nkx-6.1 gene. For example, the transgenic animal may comprise a "knock-in" of an Nkx-6.1 gene, such that the host cell genome contains an alteration that results in altered expression (e.g., increased (including ectopic) or decreased expression) of an Nkx-6.1 gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the Nkx-6.1 gene or a homozygous knock-in of the Nkx-6.1. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an Nkx-6.1 polypeptide, or may utilize the Nkx-6.1 promoter operably linked to a reporter gene. Where the introduced gene is a coding sequence, it is usually operably linked to a promoter, which may be constitutive or inducible, and other regulatory sequences required for expression in the host animal.

Specific constructs of interest include, but are not limited to, anti-sense Nkx-6.1, or a ribozyme based on an Nkx-6.1 sequence, which will block Nkx-6.1 expression, as well as expression of dominant negative Nkx-6.1 mutations, and over-expression of an Nkx-6.1 gene. A detectable marker, such as lac Z may be introduced into the Nkx-6.1 locus, where upregulation of expression of the corresponding Nkx gene will result in an easily detected change in phenotype. Constructs utilizing a promoter region of the Nkx-6.1 genes in combination with a reporter gene or with the coding region of Nkx-6.1 are also of interest. Constructs having a sequence encoding a truncated or altered (e.g, mutated) Nkx-6.1 are also of interest.

The modified cells or animals are useful in the study of function and regulation of Nkx-6.1 and, since Nkx-6.1 is thought to act upstream of Nkx-6.1, of Nkx-6.1. Such modified cells or animals are also useful in, for example, the study of the function and regulation of genes whose expression is affected by Nkx-6.1, as well as the study of the development of insulin-secreting cells in the pancreas, and the development of serotonin-secreting cells in the brain. Thus, the transgenic animals of the invention are useful in identifying downstream targets of Nkx-6.1, as such targets may have a role in the phenotypes associated with defects in Nkx-6.1.

Animals may also be used in functional studies, drug screening, etc., e.g. to determine the effect of a candidate drug on islet cell development, on β-cell function and development, on serotonin-secreting cell development, or on symptoms associated with disease or conditions associated with Nkx-6.1 defects (e.g., on symptoms associated with reduced insulin secretion (e.g., such as that associated with a diabetic syndrome, including Type 2 diabetes), symptoms associated with obesity, or on symptoms associated with reduced serotonin secretion (e.g., symptoms associated with depression). Where the transgenic animal used in the screen contains a defect in Nkx-6.1 expression (e.g., due to a knock-out of the gene), the effect of a candidate agent can be assessed by determining levels of, for example, insulin produced in the mouse relative to the levels produced in the Nkx-6.1 defective transgenic mouse and/or in wildtype mice. A series of small deletions and/or substitutions may be made in the Nkx-6;1 genes to determine the role of different exons in DNA binding, transcriptional regulation, etc. By providing expression of Nkx-6.1 protein in cells in which it is otherwise not normally produced (e.g., ectopic expression), one can induce changes in cell behavior. These animals are also useful for exploring models of inheritance of disorders associated with depression, obesity, and/or diabetes, e.g. dominant v. recessive; relative effects of different alleles and synergistic effects between Nkx-6.1 and other genes elsewhere in the genome.

DNA constructs for homologous recombination will comprise at least a portion of the Nkx-6.1 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wildtype animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well-characterized, such as C. elegans, D. melanogaster and S. cerevisiae. For example, transposon (Tc1) insertions in the nematode homolog of an Nkx-6.1 gene or a promoter region of an Nkx-6.1 gene may be made. The Nkx-6.1 gene sequences may be used to knock-out or to complement defined genetic lesions in order to determine the physiological and biochemical pathways involved in function of islet cells and/or serotonin-secreting cells. It is well known that human genes can complement mutations in lower eukaryotic models.

Production of Nkx-6.1 Polypeptides

Nkx-6.1 polypeptide-encoding nucleic acid may be employed to synthesize full-length Nkx-6.1 polypeptides or fragments thereof, particularl functional domains; DNA binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, or cells of a higher organism such as vertebrates, particularly mammals, e.g. COS 7 cells, may be used as the expression host cells. In many situations, it may be desirable to express the Nkx-6.1 genes in mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The Nkx-6.1 polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of Nkx-6.1. Antibodies may be raised to isolated peptides corresponding to these domains, or to the native protein, e.g. by immunization with cells expressing Nkx-6.1, immunization with liposomes having Nkx-6.1 polypeptides inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988.1 f desired, the MRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage "display" libraries, usually in conjunction with in vitro affinity maturation.

Isolation of Nkx-6.1 Allelic Variants and Homologues in Other Species

Other mammalian Nkx-6.1 genes can be identified and their function characterized using the Nkx-6.1 genes used in the present invention. Other mammalian Nkx-6.1 genes of interest include, but are not limited to, human, rodent (e.g, murine, or rat), bovine, feline, canine, and the like. Methods for identifying, isolating, sequencing, and characterizing an unknown gene based upon its homology to a known gene sequence are well known in the art (see, e.g., Sambrook et al., Molecular Cloning: A Laboratory Manual, CSH Press 1989.

Drug Screening

The animal models of the invention, as well as methods using the Nkx-6.1 polypeptides in vitro, can be used to identify candidate agents that affect Nkx-6.1 expression or that interact with Nkx-6.1. polypeptides. Agents of interest can include those that enhance, inhibit, regulate, or otherwise affect Nkx-6.1. activity and/or expression. Agents that enhance Nkx-6.1 activity and/or expression can be used to treat or study disorders associated with decreased Nkx-6.1 activity (e.g,. diabetes, obesity, depression), while agents that decrease Nkx-6.1. activity and/or express can be used to treat or study disorders associated with Nkx-6.1 activity (e.g, increased activity, e.g, insulinomas, expression during development). Candidate agents is meant to include synthetic molecules (e.g., small molecule drugs, peptides, or other synthetically produced molecules or compounds, as well as recombinantly produced gene products) as well as naturally-occurring compounds (e.g., polypeptides, endogenous factors present in insulin-producing and/or serotonin-producing cells, hormones, plant extracts, and the like).

Drug Screening Assays

Of particular interest in the present invention is the identification of agents that have activity in affecting Nkx-6.1 expression and/or function. Such agents are candidates for development of treatments for, for example, diabetes (especially Type 2 diabetes), depression, and obesity (in the case of Nkx-6.1.). Drug screening identifies agents that provide a replacement or enhancement for Nkx-6.1 function in affected cells. Conversely, agents that reverse or inhibit Nkx-6.1 function may provide a means to regulate insulin or serotonin production. Of particular interest are screening assays for agents that have a low toxicity for human cells.

The term "agent" as used herein describes any molecule, e.g. protein or pharmaceutical, with the capability of altering or mimicking the physiological function of Nkx-6.1. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents In Vivo

Agents can be screened for their ability to affect Nkx-6.1. expression or function or to mitigate an undesirable phenotype (e.g., a symptom) associated with an alteration in Nkx-6.1 expression or function. In a preferred embodiment, screening of candidate agents is performed in vivo in a transgenic animal described herein. Transgenic animals suitable for use in screening assays include any transgenic animal having an alteration in Nkx-6.1 expression, and can include transgenic animals having a homozygous or heterozygous knockout of an Nkx-6.1 gene, an exogenous and stably transmitted mammalian Nkx-6.1 gene sequence, and a reporter gene composed of an Nkx-6.1 promoter sequence operably linked to a reporter gene (e.g,. β-galactosidase, CAT, or other gene that can be easily assayed for expression). The transgenic animals can be either homozygous or heterozygous for the genetic alteration and, where a sequence is introduced into the animal's genome for expression, may contain multiple copies of the introduced sequence.

The candidate agent is administered to a non-human, transgenic animal having altered Nkx-6.1 expression, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing Nkx-6.1 function as appropriate (e.g., by examining expression of a reporter or fusion gene), or by assessing a phenotype associated with the Nkx-6.1 expression. For example, where the transgenic animal used in the screen contains a defect in Nkx-6.1 expression (e.g., due to a knock-out of the gene), the effect of the candidate agent can be assessed by determining levels of hormones produced in the mouse relative to the levels produced in the Nkx-6.1 defective transgenic mouse and/or in wildtype mice (e.g, by assessing levels of insulin, serotonin, and/or glucagon). Methods for assaying insulin, glucagon, and serotonin are well known in the art. Where the candidate agent affects Nkx-6.1 expression, and/or affects an Nkx-6.1-associated phenotype, in a desired manner, the candidate agent is identified as an agent suitable for use in therapy of an Nkx-6.1-associated disorder.

Screening of Candidate Agents In Vitro

In addition to screening of agents in Nkx-6.1 transgenic animals, a wide variety of in vitro assays may be used for this purpose, including labeled in vitro protein-protein binding assays, protein-DNA binding assays, electrophoretic mobility shift assays, immunoassays for protein binding, and the like. For example, by providing for the production of large amounts of Nkx-6.1 protein, one can identify ligands or substrates that bind to, modulate or mimic the action of the proteins. The purified protein may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic Nkx-6.1 function. For example, candidate agents are added to a cell that lacks functional Nkx-6.1, and screened for the ability to reproduce Nkx-6.1 activity in a functional assay.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 Proc. Natl. Acad. Sci. USA 88:9578–9582. Two-hybrid system analysis is of particular interest for exploring transcriptional activation by Nkx-6.1 proteins and to identify cDNAs encoding polypeptides that interact with Nkx-6.1.

Identified Candidate Agents

The compounds having the desired pharmacological activity may be administered in a physiologically acceptable carrier to a host for treatment of a condition attributable to a defect in Nkx-6.1 function (e.g., a disorder associated with reduced insulin levels (e.g., diabetes (Type 1 or Type 2 diabetes, particularly Type 1 diabetes); a disorder associated with reduced serotonin levels (e.g, depression and/or obesity). The compounds may also be used to enhance Nkx-6.1 function. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

Pharmacogenetics

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. In the past few years, numerous studies have established good relationships between polymorphisms in metabolic enzymes or drug targets, and both response and toxicity. These relationships can be used to individualize therapeutic dose administration.

Genotyping of polymorphic alleles is used to evaluate whether an individual will respond well to a particular therapeutic regimen. The polymorphic sequences are also used in drug screening assays, to determine the dose and specificity of a candidate therapeutic agent. A candidate Nkx-6.1 polymorphism is screened with a target therapy to determine whether there is an influence on the effectiveness in treating, for example, diabetes, depression, and/or obesity. Drug screening assays are performed as described above. Typically two or more different sequence polymorphisms are tested for response to a therapy. Therapies for diabetes currently include replacement therapy via administration of insulin and administration of drugs that increase insulin secretion (sulfonylureas) and drugs that reduce insulin resistance (such as troglitazone). Drugs currently used to treat depression include serotonin uptake blockers (e.g, prozac), while drugs currently used to treat obesity include fen-phen.

Where a particular sequence polymorphism correlates with differential drug effectiveness, diagnostic screening may be performed. Diagnostic methods have been described in detail in a preceding section. The presence of a particular polymorphism is detected, and used to develop an effective therapeutic strategy for the affected individual.

Detection of Nkx-6.1 Associated Disorders

Diagnosis of Nkx-6.1-associated disorders is performed by protein, DNA or RNA sequence and/or hybridization analysis of any convenient sample from a patient, e.g. biopsy material, blood sample, scrapings from cheek, etc. A nucleic acid sample from a patient having a disorder that may be associated with Nkx-6.1, is analyzed for the presence of a predisposing polymorphism in Nkx-6.1. A typical patient genotype will have at least one predisposing mutation on at least one chromosome. The presence of a polymorphic Nkx-6.1 sequence that affects the activity or expression of the gene product, and confers an increased susceptibility to an Nkx-6.1 associated disorder (e.g, hyperglycemia, diabetes, depression, or obesity) is considered a predisposing polymorphism. Individuals are screened by analyzing their DNA or MRNA for the presence of a predisposing polymorphism, as compared to sequence from an unaffected individual(s). Specific sequences of interest include, for example, any polymorphism that is associated with a diabetic syndrome, especially with Type 2 diabetes, or is otherwise associated with diabetes, including, but not limited to, insertions, substitutions and deletions in the coding region sequence, intron sequences that affect splicing, or promoter or enhancer sequences that affect the activity and expression of the protein.

Screening may also be based on the functional or antigenic characteristics of the protein. Immunoassays designed to detect predisposing polymorphisms in Nkx-6.1 proteins may be used in screening. Where many diverse mutations lead to a particular disease phenotype, functional protein assays can be effective screening tools.

Biochemical studies may be performed to determine whether a candidate sequence polymorphism in the Nkx-6.1 coding region or control regions is associated with disease. For example, a change in the promoter or enhancer sequence that affects expression of Nkx-6.1 may result in predisposition to diabetes, depression, and/or obesity. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like. The activity of the encoded Nkx-6.1 protein may be determined by comparison with the wild-type protein.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express Nkx-6.1 genes, such as pancreatic cells, may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. 1985 Science 239:487; a review of current techniques may be found in Sambrook, et al. Molecular Cloning: A Laboratory Manual, CSH Press 1989, pp.14.2–14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. 1990 Nucl. Acid Res. 18:2887–2890; and Delahunty et al. 1996 Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4', 5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to either a neutral Nkx-6.1 sequence (e.g, an Nkx-6.1 sequence from an unaffected individual). Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence of variant sequences. In one embodiment of the invention, an array of oligonucleotides are provided, where discrete positions on the array are complementary to at least a portion of mRNA or genomic DNA of the Nkx-6.1 locus. Such an array may comprise a series of oligonucleotides, each of which can specifically hybridize to a nucleic acid, e.g. MRNA, cDNA, genomic DNA, etc. from either the Nkx-6.1 locus. Usually such an array will include at least 2 different polymorphic sequences, i.e. polymorphisms located at unique positions within the locus, usually at least about 5, more usually at least about 10, and may include as many as 50 to 100 different polymorphisms. The oligonucleotide sequence on the array will usually be at least about 12 nt in length, may be the length of the provided polymorphic sequences, or may extend into the flanking regions to generate fragments of 100 to 200 nt in length. For examples of arrays, see Hacia et al. 1996 Nature Genetics 14:441–447; Lockhart et al. 1996 Nature Biotechnol. 14:1675–1680; and De Risi et al. 1996 Nature Genetics 14:457–460.

Antibodies specific for Nkx-6.1 polymorphisms may be used in screening inununoassays. A reduction or increase in Nkx-6.1 and/or presence of an Nkx-6.1 disorder associated polymorphism is indicative that the suspected disorder is Nkx-6.1-associated. A sample is taken from a patient suspected of having an Nkx-6.1-associated disorder. Samples, as used herein, include tissue biopsies, biological fluids, organ or tissue culture derived fluids, and fluids extracted from physiological tissues, as well as derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal Nkx-6.1 in patient cells suspected of having a predisposing polymorphism in Nkx-6.1. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and Nkx-6.1 in a lysate. Measuring the concentration of Nkx-6.1 binding in a sample or fraction thereof may be accomplished by a variety of specific assays. A conventional sandwich type assay may be used. For example, a sandwich assay may first attach Nkx-6.1-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal Nkx-6.1 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind Nkx-6.1 with sufficient specificity such that it can be distinguished from other components present. The second-antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for Nkx-6.1 as desired, conveniently using a labeling method as described for the sandwich assay.

Other diagnostic assays of interest are based on the functional properties of Nkx-6.1 proteins. Such assays are particularly useful where a large number of different sequence changes lead to a common phenotype. For example, a functional assay may be based on the transcriptional changes mediated by Nkx-6.1 gene products. Other assays may, for example, detect conformational changes, size changes resulting from insertions, deletions or truncations, or changes in the subcellular localization of Nkx-6.1 proteins.

In a protein truncation test, PCR fragments amplified from the Nkx-6.1 gene or its transcript are used as templates for in vivo transcription/translation reactions to generate protein products. Separation by gel electrophoresis is performed to determine whether the polymorphic gene encodes a truncated protein, where truncations may be associated with a loss of function.

Diagnostic screening may also be performed for polymorphisms that are genetically linked to a predisposition for diabetes, depression, and/or obesity, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. 1994 Genomics 24:225–233; Ziegle et al. 1992 Genomics 14:1026–1031; Dib et al., supra.

Microsatellite loci that are useful in the subject methods have the general formula:

U (R)$_n$ U', where

U and U' are non-repetitive flanking sequences that uniquely identify the particular locus, R is a repeat motif, and n is the number of repeats. The repeat motif is at least 2 nucleotides in length, up to 7, usually 2–4 nucleotides in length. Repeats can be simple or complex. The flanking sequences U and U'uniquely identify the microsatellite locus within the human genome. U and U' are at least about 18 nucleotides in length, and may extend several hundred bases up to about 1 kb on either side of the repeat. Within U and U', sequences are selected for amplification primers. The exact composition of the primer sequences are not critical to the invention, but they must hybridize to the flanking sequences U and U', respectively, under stringent conditions. Criteria for selection of amplification primers are as previously discussed. To maximize the resolution of size differences at the locus, it is preferable to chose a primer sequence that is close to the repeat sequence, such that the total amplification product is between 100–500 nucleotides in length.

The number of repeats at a specific locus, n, is polymorphic in a population, thereby generating individual differences in the length of DNA that lies between the amplification primers. The number will vary from at least 1 repeat to as many as about 100 repeats or more.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. 1991 Science 254:59–74. The automated sequencer is particularly useful with multiplex amplification or pooled products of separate PCR reactions. Capillary electrophoresis may also be used for fractionation. A review of capillary electrophoresis may be found in Landers, et al. 1993 BioTechniques 14:98–111. The size of the amplification product is proportional to the number of repeats (n) that are present at the locus specified by the primers. The size will be polymorphic in the population, and is therefore an allelic marker for that locus.

Therapeutic Uses of Nkx-6.1-Encoding Nucleic Acid

Nkx-6.1-encoding nucleic acid can be introduced into a cell to accomplish transformation of the cell, preferably stable transformation, and the transformed cell subsequently implanted into a subject having a disorder characterized by a deficiency in insulin and/or serotonin production (e.g., an Nkx-6.1-associated disorder), depending upon the tissue into which the transformed cell is implanted. Preferably, the host cell to be transformed and implanted in the subject is derived from the individual who will receive the transplant (e.g., to provide an autologous transplant). Where the transformed cells are to be inserted into individual (e.g., into the pancreas, liver, abdominal cavity, etc.), the cells into which the nucleic acid is introduced are preferably stem cells capable of developing into β cells within the pancreatic tissue environment, e.g., stem cells derived from gastrointestinal tissue, or cells capable of expression of insulin upon expression of the Nkx-6.1-encoding nucleic acid. Where the transformed cells are to be transplanted into the individual to provide increased serotonin production, the cells into which the nucleic acid is introduced are preferably a stem cell that is capable of developing into a serotonin-secreting cell in a brain tissue environment, or a cell capable of production of serotonin upon expression of Nkx-6.1-encoding nucleic acid.

For example, in a subject having Type 1 diabetes, gastrointestinal stem cells can be isolated from the affected subject, the cells transformed with Nkx-6.1-encoding DNA, and the transformed cells implanted in the affected subject to provide for insulin production. In a subject suffering from obesity and/or depression, a cell suitable for implantation in brain tissue is transformed with Nkx-6.1-encoding DNA, transformed cells selected and expanded, and the transformed, Nkx-6.1-expressing cells implanted into the appropriate site in brain tissue of the affected subject to provide for serotonin production.

Introduction of the Nkx-6.1-encoding nucleic acid into the cell can be accomplished according to methods well known in the art (e.g., through use of electroporation, microinjection, lipofection infection with a recombinant (preferably replication-deficient) virus, and other means well known in the art). Preferably, the Nkx-6.1-encoding nucleic acid is operably linked to a promoter that facilitates a desired level of Nkx-6.1 polypeptide expression (e.g., a promoter derived from CMV, SV40, adenovirus, or a tissue-specific or cell type-specific promoter). Transformed cells containing the Nkx-6.1-encoding nucleic acid can be selected and/or enriched via, for example, expression of a selectable marker gene present in the Nkx-6.1-encoding construct or that is present on a plasmid that is co-transfected with the Nkx-6.1-encoding construct. Typically selectable markers provide for resistance to antibiotics such as tetracycline, hygromycin, neomycin, and the like. Other markers can include thymidine kinase and the like.

The ability of the transformed cells to express the Nkx-6.1-encoding nucleic acid can be assessed by various methods known in the art. For example, Nkx-6.1 expression can be examined by Northern blot to detect mRNA which hybridizes with a DNA probe derived from the relevant gene. Those cells that express the desired gene can be further isolated and expanded in in vitro culture using methods well known in the art. The host cells selected for transformation with Nkx-6.1-encoding DNA will vary with the purpose of the ex vivo therapy (e.g., insulin production or serotonin production), the site of implantation of the cells, and other factors that will vary with a variety of factors that will be appreciated by the ordinarily skilled artisan.

Methods for engineering a host cell for expression of a desired gene product(s) and implantation or transplantation of the engineered cells (e.g., ex vivo therapy) are known in the art (see, e.g., Gilbert et al. 1993 "Cell transplantation of genetically altered cells on biodegradable polymer scaffolds in syngeneic rats," Transplantation 56:423–427). For example, for expression of a desired gene in exogenous or autologous cells and implantation of the cells for expression of the desired gene product in brain, see, e.g., Martinez-Serrano et al. 1995 "CNS-derived neural progenitor cells for gene transfer of nerve growth factor to the adult rat brain: complete rescue of axotomized cholinergic neurons after transplantation into the septum," J Neurosci 15:5668–5680; Taylor et al. 1997 "Widespread engraftment of neural progenitor and stem-like cells throughout the mouse brain," Transplant Proc 29:845–847; Snyder et al. 1997 "Potential of neural "stem-like" cells for gene therapy and repair of the degenerating central nervous system," Adv Neurol 1997;72:121–132; Snyder et al. 1996 "Gene therapy in neurology," Curr Opin Pediatr 1996 8(6):558–568; Kordower et al. 1997 "Dopaminergic transplants in patients with Parkinson's disease: neuroanatomical correlates of clinical recovery," Exp Neurol 144:41–46; Lacorazza et al. 1996 "Expression of human beta-hexosaminidase alpha-subunit gene (the gene defect of Tay-Sachs disease) in mouse brains upon engraftment of transduced progenitor cells," Nat Med 2:424–429; Martinez-Serrano et al. 1996. "Ex vivo gene transfer of brain-derived neurotrophic factor to the intact rat forebrain: neurotrophic effects on cholinergic neurons," Eur J Neurosci 8:727–735; Snyder 1995 "Immortalized neural stem cells: insights into development; prospects for gene therapy and repair," Proc Assoc Am Physicians 107:195–204; Tuszynski et al. 1996 "Gene therapy in the adult primate brain: intraparenchymal grafts of cells genetically modified to produce nerve growth factor prevent cholinergic neuronal degeneration," Gene Ther 3:305–314; and Karpati et al. 1996 "The principles of gene therapy for the nervous system," Trends Neurosci 19:49–54.

For expression of a desired gene in exogenous or autologous cells and implantation of the cells (e.g., islet cells) into pancreas, see, e.g., Docherty 1997 "Gene therapy for diabetes mellitus," Clin Sci (Colch) 92:321–330; Hegre et al. 1976 "Transplantation of islet tissue in the rat," Acta Endocrinol Suppl (Copenh) 205:257–281; Sandler et al. 1997 "Assessment of insulin secretion in vitro from microencapsulated fetal porcine islet-like cell clusters and rat, mouse, and human pancreatic islets," Transplantation 63:1712–1718; Calafiore 1997 "Perspectives in pancreatic and islet cell transplantation for the therapy of IDDM," Diabetes Care 20:889–896; Kenyon et al. 1996 "Islet cell transplantation: beyond the paradigms," Diabetes Metab Rev 12:361–372; Sandler; Chick et al. 1977 Science "Artificial pancreas using living beta cells:. effects on glucose homeostasis in diabetic rats," 197:780–782.

After expansion of the transformed cells in vitro, the cells are implanted into the mammalian subject, preferably into the tissue from which the cells were originally derived, by methods well known in the art. The number of cells implanted is a number of cells sufficient to provide for expression of levels of Nkx-6.1 sufficient to provide for enhanced levels of insulin or serotonin production. The number cells to be transplanted can be determined based upon such factors as the levels of polypeptide expression achieved in vitro, and/or the number of cells that survive implantation. Preferably the cells are implanted in an area of dense vascularization, and in a manner that minimizes evidence of surgery in the subject. The engraftment of the implant of transformed cells is monitored by examining the mammalian subject for classic signs of graft rejection, i.e., inflammation and/or exfoliation at the site of implantation, and fever.

Alternatively, Nkx-6.1-encoding nucleic acid can be delivered directly to an affected subject to provide for Nkx-6.1 expression in a target cell (e.g., a pancreatic cell, brain cell, gut cell, liver cell, or other organ cell capable of expressing Nkx-6.1 and providing production or insulin or serotonin), thereby promoting development of the cell into an insulin-producing cell (e.g., in pancreas) or a serotonin-producing cell (e.g., in brain) or to cure a defect in Nkx-6.1 expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun," or introduction of the DNA via a duct of the pancreas). For other methods of introduction of a DNA of interest into a cell in vivo, also see Bartlett et al. 1997 "Use of biolistic particle accelerator to introduce genes into isolated islets of Langerhans," Transplant Proc 29:2201–2202; Furth 1997 "Gene transfer by biolistic process," Mol Biotechnol 7:139–143; Gainer et al. 1996 "Successful biolistic transformation of mouse pancreatic islets while preserving cellular function," Transplantation 61:1567–1571; Docherty 1997 "Gene therapy for diabetes mellitus," Clin Sci (Colch) 92:321–330; Maeda et al. 1994 "Gastroenterology 1994 "Adenovirus-mediated transfer of human lipase complementary DNA to the gallbladder," 106:1638–1644.

The amount of DNA and/or the number of infectious viral particles effective to infect the targeted tissue, transform a sufficient number of cells, and provide for production of a desired level of insulin or serotonin can be readily determined based upon such factors as the efficiency of the transformation in vitro and the susceptibility of the targeted secretory gland cells to transformation. For example, the amount of DNA injected into the pancreas of a human is, for example, generally from about 1 µg to 750 mg, preferably from about 500 µg to 500 mg, more preferably from about 10 mg to 200 mg, most preferably about 100 mg. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Regardless of whether the Nkx-6.1-encoding DNA is introduced in vivo or ex vivo, the DNA (or cells expressing the DNA) can be administered in combination with other genes and other agents. In addition, Nkx-6.1-encoding DNA (or recombinant cells expressing Nkx-6.1 DNA) can be used therapeutically for disorders associated with, for example, a decrease in insulin production and/or serotonin production, but which are not associated with an alteration in Nkx-6.1 function per se. For example, an increase in Nkx-6.1 may cause an increase in insulin production in the β cells of an individual that has decreased insulin production from some other cause not related to function of Nkx-6.1.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Isolation and Sequencing of a Human Nkx-6.1 Polypeptide-Encoding Polynucleotide

To isolate a P1 human genomic clone for Nkx6.1, a set of primers were selected from the partial sequence (251 bp) of a lambda clone containing the homeodomain region of the human Nkx6.1 gene (M. German, unpublished data). Primers sequences chosen were #1: 5'-CCCTCTCCTCCCTTTTCTCC-3' (SEQ ID NO:15) and #2: 5'-AGCTGCGTGATTTTCTCGTC-3' (SEQ ID NO:16). Because of the high degree of sequence identity among various homeodomain genes, primer #2 was chosen within the homeodomain exon, and primer #1 was chosen in the adjacent intron where the sequence diverges from other homeodomain proteins. A human genomic P1 library (1.44× $10^5$ recombinants, 3 genomic equivalents, DuPont, Wilmington, Del.) was screened by PCR using primers #1 and #2. Reactions were performed under a standard condition with 1.0 mM $MgCl_2$ and 60° C. annealing temperature using an OmniGene thermal cycler (Labnet, Woodbridge, N.J.). A single P1 clone was isolated (Du28G4.1). The P1 DNA was then sequenced with an ABI automated DNA sequencer with a dye terminator kit (ABI, Foster City, Calif.) and the sequence compared to that of the hamster cDNA (Rudnick et al., 1994 Proc. Natl. Acad. Sci USA 91:12203–12207). Initially, the coding sequence of the last exon encoding the homeodomain and a stop codon, was obtained (exon III, FIG. 1B). The sequence was highly homologous to the hamster sequence (92% at the nucleotide level and 97% at the amino acid level). This result was consistent with the probability that the P1 clone contained the human Nkx6.1 gene.

Because no further information on the genomic structure, intron size or human sequence of the N-terminal region was known, a PCR strategy was devised assuming high nucleotide similarity between the N-terminal regions of the hamster and human genes. PCR primers (#3: 5'-ATGTTAGCGGTGGGGGCAATGGA-3' (SEQ ID NO:17) and #4: 5'-AGATCAGGGATCCATTTTATTGGA-3' (SEQ IDNO:18)) were chosen based on the hamster cDNA sequence. Long PCR (Expand Long, Boehringer Mannheim GmbH, Mannheim, Germany) was performed on P1 DNA of Du28G4.1 using hamster primer (primer #3 or #4) as an upper primer and primer #2 as a lower primer. PCR products obtained (approximately 4 kb and 2.2 kb, respectively) were directly sequenced and compared to the hamster sequence. Based on newly obtained human sequence, P1 sequencing was continued until the entire coding sequence and exon-intron boundaries were obtained.

The coding region of the human NKX6.1 gene was approximately 4.8 kb in size and comprised 3 exons (FIGS. 1A and 1B; translational start and stop sites are double-underlines; all translated nucleotide sequence are in upper-case letters, with the corresponding amino acid sequence (numbered on the right of the figure); sequences of the intron-exon boundaries (solid triangle) and 5'- and 3' regions of the gene are shown in lower case letters). The predicted protein sequence of the human Nkx6.1 gene included 367 amino acids (GenBank Accession U66797, U66798, U66799), 1 amino acid (3 bases) larger than the hamster Nkx6.1 protein, and had 97% overall identity to the hamster sequence. The NK decapeptide (boxed sequence in FIG. 1A) and homeodomain (underlined sequence in FIG. 1B) regions were 100% identical between the hamster and human genes, suggesting functional importance of these domains. Sizes of intron 1 and 2, determined by long PCR, were 1.5 kb and 2.1 kb, respectively. Of note, approximately 250 bp sequence in intron 2 (−303 to −46 region from a splice acceptor site of exon III) was identical to previously reported CpG island sequences (56a3 and 110a2)(1). The 5'-end of exon I and 3'-end of exon III were not mapped in this study and, thus, the possibility that additional exons may exist and encode additional 5' and/or 3' untranslated region can not be excluded.

As shown in FIGS. 1A and 1B, exon 1(SEQ ID NO:3), exon 2 (SEQ ID NO:5), and exon 3 (SEQ ID NO:7) are spliced to form the coding sequence SEQ ID NO:1, which encodes the full-length human Nkx-6.1 polypeptide (SEQ ID NO:2). The last nucleotide of exon 1 and the first two nucleotides of exon two are joined to form a codon encoding a histidine at residue position 226 in the Nkx-6.1 amino acid sequence (SEQ ID NO:2). The last three nucleotides of exon 2 encode a lysine at residue position 282, and the first three nucleotides of exon 3 encode a valine at residue position 283.

Primers 1 (SEQ ID NO:15) and 2 (SEQ ID NO:16)were also used to screen YACs from the CEPH "B" library (Research Genetics, Inc., Huntsville, Ala.). Four individual chromosome 4 YAC clones (914B4, 951G9, 981D6, and 847B3) were found to contain Nkx-6.1 Among those, three YACs (914B4, 951G9, and 981D6) were reported to overlap each other (Whitehead Institute/MIT Center for Genome Research, Human Genetic Mapping Project, Data Release 11). D4S1538, a polymorphic marker, was genetically mapped at 96 cM on chromosome 4 on the Généthon map (Dib et al., 1996 Nature 380:152–154). Nkx-6.1 and D4S1538 were colocalized on two YAC clones (914B4 and 981D6), with a maximum physical separation of 1270 kb.

FISH analysis was performed on P1 DNA from Du28G4.1 to determine the cytogenetic localization. DNA was labeled by nick-translation with biotin-11-dUPT (Rigby et al., 1977 J. Mol. Biol. 113:237–251) and hybridized to prometaphase spreads prepared from cultured phytohemagglutinin-stimulated peripheral blood lymphocytes of a male of normal karyotype (46, XY) as previously described (Lichter et al. 1988 Hum. Genet. 80:224–234; Yunis 1976 Science 191:1268–1270). For fluorochronie detection, slides were incubated with fluorescein-isothiocyantate (FITC)-conjugated avidin DCS (Vector Laboratories, Calif.), amplified by incubation in 5 µg/ml FITC-conjugated goat anti-avidin D antibodies (Vector Laboratories), followed by a second layer in fluorescein-avidin DCS. Metaphases were counterstained in a final wash with 4,6-diamidino-2-phenylindole (200 ng/ml) and propidium iodide (200 ng/ml). Fifty prometaphase spreads were analyzed. Following FISH, cytogenetic banding was performed by Giemsa staining using standard methods. This analysis determined that Nkx-6.1 is localized to 4q21.2-q22.

Both rapid amplification of cDNA ends (RACE) and RNase protection assays, both of which are well known in the art, were used to identify the transcriptional start site of the murine Nkx-6.1 gene. Using RACE, the 5' end of the murine Nkx-6.1 cDNA was extended using reverse transcriptase and PCR. The resulting cDNA was then sequenced to identify the promoter region 5' of the cDNA coding sequence of Nkx-6.1 RNase protection assays were performed by hybridizing mRNA from cells expressing murine Nkx-6.1 with a labeled RNA copy of genomic murine Nkx-6.1 DNA that includes the putative regions of transcription initiation. Enzymes that degrade single stranded RNA, but not RNA-RNA hybrids were added to the mixture. The protected double-stranded RNAs were then separated by gel electrophoresis to measure the length of the protected fragments, which in turn identified the transcriptional start sites of murine Nkx-6.1.

Analysis of the RACE and RNase protection assay data indicated that the Nkx-6.1 promoter does not contain a classic TATAA box. Thus, like many TATAA-less promoters, the Nkx-6.1 promoter has a stuttering transcription initiation site. Four main start sites were identified at −1049, −974, −969, and −966 bp relative to the start of the coding sequence of the murine Nkx-6.1 gene. The 5' untranslated portion of the transcript contains no introns. The promoter region of Nkx-6.1 is highly conserved between mice and humans. FIGS. 4A and 4B illustrates this point by providing an alignment of the available human genomic sequence with the promoter sequence of murine Nkx-6.1. The human and murine sequences provided both end at the last of the four start sites (i.e., the 3' end of SEQ ID NOS:19, 20, and 21 include the sequence of the most' 3' start site, which is '966 bp from the Nkx-6.1 coding sequence). Only nucleotides 1801–2990 of the murine Nkx-6.1 promoter sequence (SEQ ID NO:21) are shown; the entire murine Nkx-6.1 promoter sequence is provided in the sequence listing as (SEQ ID NO:19). Hyphens are inserted within the sequences to provide for optimal alignment) are shown Thus the human sequence show in FIGS. 4A and 4B (SEQ ID NO:20) is contained within the human Nkx-6.1 promoter sequence.

Example 2

Heterozygous Nkx-6.1 Knock-Out Transgenic Mice

To determine the function of Nkx-6.1 in development, mice heterozygous for an Nkx-6.1 mutation, as well as mice homozygous for a null mutation of Nkx-6.1 (see Example 3 below) were generated using standard gene targeting techniques. Briefly, an Nkx-6.1 gene targeting vector was constructed by isolating a genomic DNA clone containing the entire Nkx-6.1 gene from a 129J mouse genomic library using PCR primers based on the rat homeobox and NK-2 box (Price et al. 1992 Neuron 8:241–255). A single clone was obtained that included the entire coding region of the Nkx-6.1 gene. This genomic clone was mapped extensively with restriction enzymes and Southern analysis. This mapping data provided sufficient information for the construction of an Nkx-6.1 gene replacement vector.

A null mutation of Nkx-6.1 was generated by replacing a portion of the coding sequence of Nkx-6.1, including the translation start site, with a PGK-neo cassette. Approximately 1 kb of 3' Nkx-6.1 genomic sequence and 5 kb of 5' Nkx-6.1 genomic sequences flanked the deletion in order to facilitate homologous recombination events. The recombinant plasmid also contained a herpes simplex virus thymidine kinase (tk) gene flanking the genomic DNA to permit selection against nonhomologous recombination events.

The Nkx-6.1 targeting DNA vector was electroporated into mouse (129J) embryonic stem (ES) cells using the positive-negative selection strategy for homologous recombination (Mansour, et al. 1988 Nature 336:348–352). Candidate ES clones were screened for homologous recombination by Southern analysis of the genomic DNA to detect homologous integration events. The ES cells were then implanted into blastocysts, chimeras identified, and heterozygotes produced as described above.

Correctly targeted ES cells were injected into C57BL/6J host blastocysts to generate chimeric mice. Chimeric males that transmit the targeted DNA through the germline will be bred to produce F1 mice that are heterozygous for each of the mutant alleles. Inbreeding between the heterozygous mice will be used to produce homozygous mutant animals. The resulting heterozygote mice were bred for generation of a homozygous mutants.

Heterozygous Nkx-6.1 knock-out transgenics survived to adulthood, were fertile, and have an apparently normal phenotype in all assays tested. The Nkx-6.1 heterozygous knock-outs may have decreased insulin and insulin mRNA levels compared to wildtype mice. Obese heterozygotes have been observed at 1 year after birth.

Example 3

Homozygous Nkx-6.1 Knock-Out Transgenic Mice

Homozygous Nkx-6.1 knock-out transgenic mice were produced by crossing the heterozygous Nkx-6.1 knock-out transgenic mice described in Example 2.

The pancreas of the homozygous knock-out (null) Nkx-6.1 transgenic mice had almost no β-cells, but other islet cells appeared normal. The null Nkx-6.1 mice died immediately after birth (within about 1 hour) and exhibited severe neurological defects, including decreased movement and defects in motor neurons.

These data show that Nkx-6.1 plays a critical role in islet development, insulin production, and neural development.

Example 4

Heterozygous Nkx-2.2 Knock-Out Transgenic Mice

To determine the function of Nkx-2.2 in development, mice heterozygous for an Nkx-2.2 mutation, as well as mice homozygous for a null mutation of Nkx-2.2 (see Example 2 below) were generated using standard gene targeting techniques. Briefly, an Nkx-2.2 gene targeting vector was constructed by isolating several genomic DNA clones containing the entire Nkx-2.2 gene from a 129J mouse genomic library using PCR primers based on the rat homeobox and NK-2 box (Price et al. 1992 Neuron 8:241–255). Two partially overlapping genomic clones were isolated; each clone contained an approximately 14 kb insert containing the Nkx-2.2 gene in a relatively central position within each clone. These genomic clones were mapped extensively with restriction enzymes and Southern analysis. This mapping data provided sufficient information for the construction of an Nkx-2.2 gene replacement vector.

A null mutation of Nkx-2.2 was generated by replacing all of the coding sequence of Nkx-2.2, including the homeobox region, with a PGK-neo cassette. Approximately 6 kb of 3' and 4 kb of 5' Nkx-2.2 genomic sequences flanked the deletion in order to facilitate homologous recombination events. The recombinant plasmid also contained a herpes simplex virus thymidine kinase (tk) gene flanking the genomic DNA to permit selection against nonhomologous recombination events.

The Nkx-2.2 targeting DNA vector was electroporated into mouse (129J) embryonic stem (ES) cells using the positive-negative selection strategy for homologous recombination (Mansour, et al. 1988 Nature 336:348–352). Candidate ES clones were screened for homologous recombination by Southern analysis of the genomic DNA. Four clones contained the mutant allele and had undergone a single homologous integration at the Nkx-2.2 locus.

Correctly targeted ES cells were injected into C57BL/6J host blastocysts to generate chimeric mice. Chimeric males that transmit the targeted DNA through the germline will be bred to produce F1 mice that are heterozygous for each of the mutant alleles. Inbreeding between the heterozygous mice will be used to produce homozygous mutant animals.

Heterozygous Nkx-2.2 knock-out transgenics survived to adulthood, were fertile, and have an apparently normal phenotype in all assays tested. The Nkx-2.2 heterozygous knock-outs may have decreased insulin and insulin mRNA levels compared to wildtype mice. Obese heterozygotes have been observed at 1 year after birth.

Example 5

Homozygous Nkx-2.2 Knock-Out Transgenic Mice

Homozygous Nkx-2.2 knock-out transgenic mice were produced by crossing the heterozygous transgenic mice described in Example 4.

Homozygous knock-out (null) Nkx-2.2. mice were grossly indistinguishable from their wildtype and heterozygous littermates at birth. However, by the third day after birth, the homozygous mutant animals displayed growth retardation and did not survive longer than six days postnatally. The gross morphology of the homozygous null Nkx-2.2 transgenic mice appeared normal. However, histological analysis revealed a general reduction in islet cell mass; the exocrine cells appeared unaffected. Immunohistochemical analysis showed that there was a remarkable defect in islet cell development. Insulin was undetectable in comparative studies between mutant and wildtype littermates. In addition, the number of cells producing glucagon were reduced, and the level of glucagon per cell was diminished. Glucokinase expression in the pancreas was undetectable. Radioimmunoassays confirmed the immunohistochemical results. Insulin content in the pancreas of Nkx-2.2 null mice was undetectable, and glucagon content was reduced at least 20-fold relative to wildtype mice.

A large population of cells within clusters of the pancreas did not produce any of the four endocrine hormones (insulin, glucagon, somatostatin, and pancreatic polypeptide). Because expression of pancreatic polypeptide and somatostatin in the pancreas as a whole was normal, these non-endocrine producing cells, which appeared within normal size islets, may be precursors to the glucagon-producing α or insulin-producing β cells. The null Nkx-2.2 animals still exhibited roughly normal islet amyloid polypeptide (amylin) expression. A summary of the molecular characteristics of islets in the Nkx-2.2 null transgenic animals (as determined by immunohistochemistry) is provided in Table 2 below.

TABLE 2

Islet Molecular Characteristics in the Nkx-2.2 Mutant - Summary of Immunohistochemistry Results

| Endocrine Hormones | |
| --- | --- |
| Insulin | undetectable |
| Glucagon | reduced |
| Somatostatin | normal |
| Pancreatic polypeptide | reduced |
| β Cell Markers | |
| Glucokinase | undetectable |
| Glut2 | undetectable |
| PC1/PC3 | normal |
| Amylin | normal |
| Transcription Factors | |
| Pax6 | normal/reduced |
| Pdx1 | reduced |
| Nkx-6.1 (putative transcription factor) | undetectable |

In addition to the defects in the pancreas, the homozygous Nkx-2.2 knock-out transgenic mice also exhibited neural defects. A subset of serotonin-producing cells in the brain were decreased in number relative to the number of serotonin-producing cells in wildtype mice. These data show that Nkx-2.2 plays a critical role in islet development, insulin and glucagon synthesis, and in development of serotonin-producing cells in the brain.

The invention now being fully described, it will be apparent to one of ordinary skill in the art that many changes and modifications can be made thereto without departing from the spirit or scope of the appended claims.

What is claimed is:

1. An isolated polynucleotide, or complement thereof, comprising a polynucleotide sequence that is at least 95% identical to a polynucleotides sequence of nucleotides 1–1101 of SEQ ID NO:1, wherein said isolated polynucleotide encodes a polypeptide which promotes development of pancreatic beta cells.

2. A recombinant expression vector comprising tho polynucleotide sequence of claim 1.

3. An insolated recombinant host cell containing the polynucleotide sequence of claim 1.

4. A method for producing a human Nkx-6.1 polypeptide, the method comprising the steps of:
   a) culturing a recombinant host cell containing a polynucleotide sequence of claim 1 under conditions suitable for the expression of the encoded polypeptide; and
   b) recovering the expressed polypeptide from the host cell culture.

5. A hybridization probe, or complement thereof, consisting of a polynucleotide sequence of SEQ ID NO: 3.

6. An isolated polynucleotide, or complement thereof, comprising a polynucleotide sequence encoding an amino acid sequence of SEQ ID NO:2.

7. A hybridization probe, or complement thereof, consisting of a polynucleotide sequence of SEQ ID NO: 5.

8. A hybridization prove, or complement thereof, consisting of a polynucleotide sequence of SEQ ID NO: 7.

* * * * *

UNITED STATES PATENT AND TRADEMARK OFFICE
CERTIFICATE OF CORRECTION

PATENT NO.    : 6,436,667 B1
DATED         : August 20, 2002
INVENTOR(S)   : German, Michael S., et al.

It is certified that error appears in the above-identified patent and that said Letters Patent is hereby corrected as shown below:

Column 53,
Line 28, please change "polynucleotides" to -- polynucleotide --.
Line 32, please change "tho" to -- the --.

Column 54,
Line 36, please change "prove" to -- probe --.

Signed and Sealed this

Eighteenth Day of March, 2003

JAMES E. ROGAN
*Director of the United States Patent and Trademark Office*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 1104 base pairs
       (B) TYPE: nucleic acid
       (C) STRANDEDNESS: single
       (D) TOPOLOGY: linear (ix) FEATURE:
       (A) NAME/KEY: Coding Sequence
       (B) LOCATION: 1...1101
       (D) OTHER INFORMATION:

(xi) SEQUENCE DESCRIPTION: SEQ ID NO:1:

```
ATG TTA GCG GTG GGG GCA ATG GAG GGC ACC CGG CAG AGC GCA TTC CTG        48
Met Leu Ala Val Gly Ala Met Glu Gly Thr Arg Gln Ser Ala Phe Leu
 1               5                  10                  15

CTC AGC AGC CCT CCC CTG GCC GCC CTG CAC AGC ATG GCC GAG ATG AAG        96
Leu Ser Ser Pro Pro Leu Ala Ala Leu His Ser Met Ala Glu Met Lys
                20                  25                  30

ACC CCG CTG TAC CCT GCC GCG TAT CCC CCG CTG CCT GCC GGC CCC CCC       144
Thr Pro Leu Tyr Pro Ala Ala Tyr Pro Pro Leu Pro Ala Gly Pro Pro
            35                  40                  45

TCC TCC TCG TCC TCG TCG TCG TCC TCC TCG TCG CCC TCC CCG CCT CTG       192
Ser Ser Ser Ser Ser Ser Ser Ser Ser Ser Ser Pro Ser Pro Pro Leu
        50                  55                  60

GGC ACC CAC AAC CCA GGC GGC CTG AAG CCC CCG GCC ACG GGG GGG CTC       240
Gly Thr His Asn Pro Gly Gly Leu Lys Pro Pro Ala Thr Gly Gly Leu
65                  70                  75                  80

TCA TCC CTC GGC AGC CCC CCG CAG CAG CTC TCG GCC GCC ACC CCA CAC       288
Ser Ser Leu Gly Ser Pro Pro Gln Gln Leu Ser Ala Ala Thr Pro His
                85                  90                  95

GGC ATC AAC AAT ATC CTG AGC CGG CCC TCC ATG CCC GTG GCC TCG GGG       336
Gly Ile Asn Asn Ile Leu Ser Arg Pro Ser Met Pro Val Ala Ser Gly
            100                 105                 110

GCC GCC CTG CCC TCC GCC TCC GGT TCC GGT TCC TCC TCC TCC TCT TCC       384
Ala Ala Leu Pro Ser Ala Ser Gly Ser Gly Ser Ser Ser Ser Ser Ser
        115                 120                 125

TCG TCC GCC TCT GCC TCC TCC GCC TCT GCC GCC GCC GCG GCT GCT GCC       432
Ser Ser Ala Ser Ala Ser Ser Ala Ser Ala Ala Ala Ala Ala Ala Ala
    130                 135                 140

GCG GCC GCA GCC GCC GCC TCA TCC CCG GCG GGG CTG CTG GCC GGA CTG       480
Ala Ala Ala Ala Ala Ala Ser Ser Pro Ala Gly Leu Leu Ala Gly Leu
145                 150                 155                 160

CCA CGC TTT AGC AGC CTG AGC CCG CCG CCG CCG CCG CCC GGG CTC TAC       528
Pro Arg Phe Ser Ser Leu Ser Pro Pro Pro Pro Pro Pro Gly Leu Tyr
                165                 170                 175

TTC AGC CCC AGC GCC GCG GCC GTG GCC GCC GTG GGC CGG TAC CCC AAG       576
Phe Ser Pro Ser Ala Ala Ala Val Ala Ala Val Gly Arg Tyr Pro Lys
            180                 185                 190

CCG CTG GCT GAG CTG CCT GGC CGG ACG CCC ATC TTC TGG CCC GGA GTG       624
Pro Leu Ala Glu Leu Pro Gly Arg Thr Pro Ile Phe Trp Pro Gly Val
        195                 200                 205

ATG CAG AGC CCG CCC TGG AGG GAC GCA CGC CTG GCC TGT ACC CCT CAT       672
Met Gln Ser Pro Pro Trp Arg Asp Ala Arg Leu Ala Cys Thr Pro His
    210                 215                 220
```

-continued

```
CAA GGA TCC ATT TTG TTG GAC AAA GAC GGG AAG AGA AAA CAC ACG AGA      720
Gln Gly Ser Ile Leu Leu Asp Lys Asp Gly Lys Arg Lys His Thr Arg
225                 230                 235                 240

CCC ACT TTT TCC GGA CAG CAG ATC TTC GCC CTG GAG AAG ACT TTC GAA      768
Pro Thr Phe Ser Gly Gln Gln Ile Phe Ala Leu Glu Lys Thr Phe Glu
                245                 250                 255

CAA ACA AAA TAC TTG GCG GGG CCC GAG AGG GCT CGT TTG GCC TAT TCG      816
Gln Thr Lys Tyr Leu Ala Gly Pro Glu Arg Ala Arg Leu Ala Tyr Ser
            260                 265                 270

TTG GGG ATG ACA GAG AGT CAG GTC AAG GTC TGG TTC CAG AAC CGC CGG      864
Leu Gly Met Thr Glu Ser Gln Val Lys Val Trp Phe Gln Asn Arg Arg
        275                 280                 285

ACC AAG TGG AGG AAG AAG CAC GCT GCC GAG ATG GCC ACG GCC AAG AAG      912
Thr Lys Trp Arg Lys Lys His Ala Ala Glu Met Ala Thr Ala Lys Lys
    290                 295                 300

AAG CAG GAC TCG GAG ACA GAG CGC CTC AAG GGG GCC TCG GAG AAC GAG      960
Lys Gln Asp Ser Glu Thr Glu Arg Leu Lys Gly Ala Ser Glu Asn Glu
305                 310                 315                 320

GAA GAG GAC GAC GAC TAC AAT AAG CCT CTG GAT CCC AAC TCG GAC GAC     1008
Glu Glu Asp Asp Asp Tyr Asn Lys Pro Leu Asp Pro Asn Ser Asp Asp
                325                 330                 335

GAG AAA ATC ACG CAG CTG TTG AAG AAG CAC AAG TCC AGC AGC GGC GGC     1056
Glu Lys Ile Thr Gln Leu Leu Lys Lys His Lys Ser Ser Ser Gly Gly
            340                 345                 350

GGC GGC GGC CTC CTA CTG CAC GCG TCC GAG CCG GAG AGC TCA TCC TGA     1104
Gly Gly Gly Leu Leu Leu His Ala Ser Glu Pro Glu Ser Ser Ser
        355                 360                 365
```

(2) INFORMATION FOR SEQ ID NO:2:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
            85                  90                  95

Gly Ile Asn Asn Ile Leu Ser Arg Pro Ser Met Pro Val Ala Ser Gly
        100                 105                 110

Ala Ala Leu Pro Ser Ala Ser Gly Ser Gly Ser Ser Ser Ser Ser Ser
    115                 120                 125

Ser Ser Ala Ser Ala Ser Ser Ala Ser Ala Ala Ala Ala Ala Ala
130                 135                 140

Ala Ala Ala Ala Ala Ala Ser Ser Pro Ala Gly Leu Leu Ala Gly Leu
```

```
                           145                 150                 155                     160
Pro Arg Phe Ser Ser Leu Ser Pro Pro Pro Pro Gly Leu Tyr
                    165                 170             175

Phe Ser Pro Ser Ala Ala Ala Val Ala Val Gly Arg Tyr Pro Lys
                180             185                 190

Pro Leu Ala Glu Leu Pro Gly Arg Thr Pro Ile Phe Trp Pro Gly Val
            195                 200                 205

Met Gln Ser Pro Pro Trp Arg Asp Ala Arg Leu Ala Cys Thr Pro His
        210                 215                 220

Gln Gly Ser Ile Leu Leu Asp Lys Asp Gly Lys Arg Lys His Thr Arg
225                 230                 235                     240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285

Thr Lys Trp Arg Lys Lys His Ala Ala Glu Met Ala Thr Ala Lys Lys
    290                 295                 300

Lys Gln Asp Ser Glu Thr Glu Arg Leu Lys Gly Ala Ser Glu Asn Glu
305                 310                 315                     320

Glu Glu Asp Asp Asp Tyr Asn Lys Pro Leu Asp Pro Asn Ser Asp Asp
                325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
        355                 360                 365

(2) INFORMATION FOR SEQ ID NO:3:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...669
        (D) OTHER INFORMATION:

(xi) SEQUENCE DESCRIPTION: SEQ ID NO:3:

ATG TTA GCG GTG GGG GCA ATG GAG GGC ACC CGG CAG AGC GCA TTC CTG        48
Met Leu Ala Val Gly Ala Met Glu Gly Thr Arg Gln Ser Ala Phe Leu
 1               5                  10                  15

CTC AGC AGC CCT CCC CTG GCC GCC CTG CAC AGC ATG GCC GAG ATG AAG        96
Leu Ser Ser Pro Pro Leu Ala Ala Leu His Ser Met Ala Glu Met Lys
                20                  25                  30

ACC CCG CTG TAC CCT GCC GCG TAT CCC CCG CTG CCT GCC GGC CCC CCC       144
Thr Pro Leu Tyr Pro Ala Ala Tyr Pro Pro Leu Pro Ala Gly Pro Pro
            35                  40                  45

TCC TCC TCG TCC TCG TCG TCG TCC TCC TCG TCG CCC TCC CCG CCT CTG       192
Ser Ser Ser Ser Ser Ser Ser Ser Ser Ser Pro Ser Pro Pro Leu
        50                  55                  60

GGC ACC CAC AAC CCA GGC GGC CTG AAG CCC CCG GCC ACG GGG GGG CTC       240
Gly Thr His Asn Pro Gly Gly Leu Lys Pro Pro Ala Thr Gly Gly Leu
65                  70                  75                  80

TCA TCC CTC GGC AGC CCC CCG CAG CAG CTC TCG GCC GCC ACC CCA CAC       288
Ser Ser Leu Gly Ser Pro Pro Gln Gln Leu Ser Ala Ala Thr Pro His
```

```
                    85                  90                      95
GGC ATC AAC AAT ATC CTG AGC CGG CCC TCC ATG CCC GTG GCC TCG GGG        336
Gly Ile Asn Asn Ile Leu Ser Arg Pro Ser Met Pro Val Ala Ser Gly
                100                 105                 110

GCC GCC CTG CCC TCC GCC TCG CCC TCC GGT TCC TCC TCC TCC TCT TCC        384
Ala Ala Leu Pro Ser Ala Ser Pro Ser Gly Ser Ser Ser Ser Ser Ser
            115                 120                 125

TCG TCC GCC TCT GCC TCC TCC GCC TCT GCC GCC GCC GCG GCT GCT GCC        432
Ser Ser Ala Ser Ala Ser Ser Ala Ser Ala Ala Ala Ala Ala Ala Ala
        130                 135                 140

GCG GCC GCA GCC GCC GCC TCA TCC CCG GCG GGG CTG CTG GCC GGA CTG        480
Ala Ala Ala Ala Ala Ala Ser Ser Pro Ala Gly Leu Leu Ala Gly Leu
145                 150                 155                 160

CCA CGC TTT AGC AGC CTG AGC CCG CCG CCG CCG CCC GGG CTC TAC            528
Pro Arg Phe Ser Ser Leu Ser Pro Pro Pro Pro Pro Gly Leu Tyr
                165                 170                 175

TTC AGC CCC AGC GCC GCG GCC GTG GCC GCC GTG GGC CGG TAC CCC AAG        576
Phe Ser Pro Ser Ala Ala Ala Val Ala Ala Val Gly Arg Tyr Pro Lys
                180                 185                 190

CCG CTG GCT GAG CTG CCT GGC CGG ACG CCC ATC TTC TGG CCC GGA GTG        624
Pro Leu Ala Glu Leu Pro Gly Arg Thr Pro Ile Phe Trp Pro Gly Val
        195                 200                 205

ATG CAG AGC CCG CCC TGG AGG GAC GCA CGC CTG GCC TGT ACC CCT C          670
Met Gln Ser Pro Pro Trp Arg Asp Ala Arg Leu Ala Cys Thr Pro
    210                 215                 220

(2) INFORMATION FOR SEQ ID NO:4:

(i) SEQUENCE CHARACTERISTICS:
        (A) LENGTH: 223 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Pro Ser Pro Pro Leu
50                  55                  60

Gly Thr His Asn Pro Gly Gly Leu Lys Pro Pro Ala Thr Gly Leu
65                  70                  75                  80

Ser Ser Leu Gly Ser Pro Pro Gln Gln Leu Ser Ala Ala Thr Pro His
            85                  90                  95

Gly Ile Asn Asn Ile Leu Ser Arg Pro Ser Met Pro Val Ala Ser Gly
                100                 105                 110

Ala Ala Leu Pro Ser Ala Ser Pro Ser Gly Ser Ser Ser Ser Ser Ser
            115                 120                 125

Ser Ser Ala Ser Ala Ser Ser Ala Ser Ala Ala Ala Ala Ala Ala Ala
        130                 135                 140

Ala Ala Ala Ala Ala Ala Ser Ser Pro Ala Gly Leu Leu Ala Gly Leu
145                 150                 155                 160
```

```
Pro Arg Phe Ser Ser Leu Ser Pro Pro Pro Pro Gly Leu Tyr
            165                 170                 175

Phe Ser Pro Ser Ala Ala Val Ala Ala Val Gly Arg Tyr Pro Lys
            180                 185                 190

Pro Leu Ala Glu Leu Pro Gly Arg Thr Pro Ile Phe Trp Pro Gly Val
        195                 200                 205

Met Gln Ser Pro Pro Trp Arg Asp Ala Arg Leu Ala Cys Thr Pro
        210                 215                 220
```

(2) INFORMATION FOR SEQ ID NO:5:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 3...173
        (D) OTHER INFORMATION:

(xi) SEQUENCE DESCRIPTION: SEQ ID NO:5:

```
AT CAA GGA TCC ATT TTG TTG GAC AAA GAC GGG AAG AGA AAA CAC ACG      47
   Gln Gly Ser Ile Leu Leu Asp Lys Asp Gly Lys Arg Lys His Thr
   1               5                   10                  15

AGA CCC ACT TTT TCC GGA CAG CAG ATC TTC GCC CTG GAG AAG ACT TTC     95
Arg Pro Thr Phe Ser Gly Gln Gln Ile Phe Ala Leu Glu Lys Thr Phe
                20                  25                  30

GAA CAA ACA AAA TAC TTG GCG GGG CCC GAG AGG GCT CGT TTG GCC TAT    143
Glu Gln Thr Lys Tyr Leu Ala Gly Pro Glu Arg Ala Arg Leu Ala Tyr
            35                  40                  45

TCG TTG GGG ATG ACA GAG AGT CAG GTC AAG                            173
Ser Leu Gly Met Thr Glu Ser Gln Val Lys
        50                  55
```

(2) INFORMATION FOR SEQ ID NO:6:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Gln Gly Ser Ile Leu Leu Asp Lys Asp Gly Lys Arg Lys His Thr Arg
1               5                   10                  15

Pro Thr Phe Ser Gly Gln Gln Ile Phe Ala Leu Glu Lys Thr Phe Glu
            20                  25                  30

Gln Thr Lys Tyr Leu Ala Gly Pro Glu Arg Ala Arg Leu Ala Tyr Ser
        35                  40                  45

Leu Gly Met Thr Glu Ser Gln Val Lys
    50                  55
```

(2) INFORMATION FOR SEQ ID NO:7:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ix) FEATURE:
              (A) NAME/KEY: Coding Sequence
              (B) LOCATION: 1...258
              (D) OTHER INFORMATION:

(xi) SEQUENCE DESCRIPTION: SEQ ID NO:7:

```
GTC TGG TTC CAG AAC CGC CGG ACC AAG TGG AGG AAG AAG CAC GCT GCC      48
Val Trp Phe Gln Asn Arg Arg Thr Lys Trp Arg Lys Lys His Ala Ala
1               5                   10                  15

GAG ATG GCC ACG GCC AAG AAG AAG CAG GAC TCG GAG ACA GAG CGC CTC      96
Glu Met Ala Thr Ala Lys Lys Lys Gln Asp Ser Glu Thr Glu Arg Leu
            20                  25                  30

AAG GGG GCC TCG GAG AAC GAG GAA GAG GAC GAC GAC TAC AAT AAG CCT     144
Lys Gly Ala Ser Glu Asn Glu Glu Glu Asp Asp Asp Tyr Asn Lys Pro
        35                  40                  45

CTG GAT CCC AAC TCG GAC GAC GAG AAA ATC ACG CAG CTG TTG AAG AAG     192
Leu Asp Pro Asn Ser Asp Asp Glu Lys Ile Thr Gln Leu Leu Lys Lys
    50                  55                  60

CAC AAG TCC AGC AGC GGC GGC GGC GGC GGC CTC CTA CTG CAC GCG TCC     240
His Lys Ser Ser Ser Gly Gly Gly Gly Gly Leu Leu Leu His Ala Ser
65                  70                  75                  80

GAG CCG GAG AGC TCA TCC TGA                                         261
Glu Pro Glu Ser Ser Ser
                85
```

(2) INFORMATION FOR SEQ ID NO:8:

(i) SEQUENCE CHARACTERISTICS:
              (A) LENGTH: 86 amino acids
              (B) TYPE: amino acid
              (C) STRANDEDNESS: single
              (D) TOPOLOGY: linear (ii) MOLECULE TYPE: protein (v) FRAGMENT TYPE: internal (xi) SEQUENCE DESCRIPTION: SEQ ID NO:8:

```
Val Trp Phe Gln Asn Arg Arg Thr Lys Trp Arg Lys Lys His Ala Ala
1               5                   10                  15

Glu Met Ala Thr Ala Lys Lys Lys Gln Asp Ser Glu Thr Glu Arg Leu
            20                  25                  30

Lys Gly Ala Ser Glu Asn Glu Glu Glu Asp Asp Asp Tyr Asn Lys Pro
        35                  40                  45

Leu Asp Pro Asn Ser Asp Asp Glu Lys Ile Thr Gln Leu Leu Lys Lys
    50                  55                  60

His Lys Ser Ser Ser Gly Gly Gly Gly Gly Leu Leu Leu His Ala Ser
65                  70                  75                  80

Glu Pro Glu Ser Ser Ser
                85
```

(2) INFORMATION FOR SEQ ID NO:9:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (xi) SEQUENCE DESCRIPTION: SEQ ID NO:9:

CCTCGCTGCA AGGCTACGGT CTCCGGCGTG GCCGTGGG                            38

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

```
GTGAGTACTA CCACCCGCGC CCCGA                                       25
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

```
TCTCGTTGTT TATTGGTTCT CACAG                                       25
```

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

```
GTGAGTGGAC CTTGCATACC TGGAG                                       25
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

```
TCTCCTCCCT TTTCTCCGCC TCAG                                        24
```

(2) INFORMATION FOR SEQ ID NO:14:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:14:

```
ACGCCGCCGC CGCCGCACCC TTCCCGGCTC CGGCCTCCAC CTCTGGGGCC GCGAGGG     57
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

```
CCCTCTCCTC CCTTTTCTCC                                             20
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

AGCTGCGTGA TTTTCTCGTC                                                     20

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:17:

ATGTTAGCGG TGGGGGCAAT GGA                                                 23

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

AGATCAGGGA TCCATTTTAT TGGA                                                24

(2) INFORMATION FOR SEQ ID NO:19:

(i) SEQUENCE CHARACTERISTICS:
        (A) LENGTH: 2990 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGATCCACCT TCCACACCTC TCCCTGTGAC CCCCTCCTGC AACCTCCGAT TGCCCAACA           60

GCTTTCATTT ATTTTTAATT AAAATGCAAA TCAATCGCTT TCAAGTAGAG CCTTGCCCTC         120

TCCAATATAT AGCTGTATAC ATATAGAAGC GTGGTGTTGA GATGAGCCGG TCGGTTGCTT         180

CCTCTGCTAC TTGTTTGGAA GGGCCCCCGG CTTTATTAGG AAGTGTGCGC AAGAGTTAGG         240

AGGTCCCCAA GGAAAAACAA TCAGGAGCCT CAAGAGGGTT TGAAAGCAGC AAACCCTGGG         300

CCCACAAGGC AGGCAGGCCC TGCCACACCC ATTGCAGCTC GCCTGGAACC CCGGGCCGAA         360

GAGTGGAGGG CAGGGTGACC TCTTCCCGAC TGAGCCCAGC AGCTCACACT CCTGGGATCC         420

TGGGGGCAGA TCCCAGACAG CACCTGGCTA GAGGCACCCG CCTTTCTTCA GAGGCGGGTG         480

GGATGAGTCG GAAAACAAGC TGCCATTGCC GCTGCCGCAA TGAAGAATTT AGACACCCCT         540

CAAGGATCGA GGTACACAGT CCCCATCATT TTTTATTGTT AGAATTGGGA ATCATACTAT         600

TTAAATTATG AATTATGAAT GACAGAGACT CAACGGATGA GATGTCTTCA TTTCAAAACC         660

AGCTTTGTAA CTACGGAGCA CAGTTAAGTT GGAGTTGACT CACTCACTCT CTCTCTCTCT         720

CTCTCTCTCT CTCTCTCTCT CTCTCTCTCC TCCCCCTTCC CCACTTTCTC TGTCTTTCTC         780

TGTGTCTCTG TCTTTCTCTT TGTCTATCTC TCTGTCTTTC TCTGTCTCTC TGTCCCTGTG         840

TGTCCTTGTC TGTCTTTCGC TGTGTCTCTG TCCGTCTCTC TGTTTCCGTC TCTCTCCGGT         900

```
CTATTTTCTT TTTTGACACC CCCTCCCCAA TACCAGATAC TAAGTTCTCA ATAGAAAAAA      960

AAAACTGATC AATTTACCAA CCAATTCCCC ATTACAGTAA CTACAAAGAT AGCTACTTTT     1020

GAGGAAAGAA CTTCCAATAC ACTTAGGTTC GGTTTTCTCA GTTCCTACCT AGTCCCTTTA     1080

CCCGGTGGAC ATGAGCAGAT CGTAGGAGGC CCAAAATTCG AGCTCTGGCT GATCGTGTGC     1140

CACGGAGGAA ATGCTGGGTC CGAGTGAGAG TAGTTTGTGA GGAAGCCAGA GGCATTGAAA     1200

TTCCAGCGGC AGAAACAGAG CCGGGGCTGG CCCGCCACTG TCCGCTTCAC GAAATTGGCT     1260

GGCAGCTCTT CTCGGGTTTA GGTAGCAGAG GGCTGGCGTG GAAGCGCAGA CAGCACCCAC     1320

TTTAGCTCTC CCCGGAGCCT AGAGACTGGC AGGCCGCTTA GCATATCTCC CACCCGTGCA     1380

GAGCCCCACC TTTCCCAGGG TCAGATCTAA ACTCTACGGA ATGATGGCAT TAACCAAGTC     1440

TTGAAGTTTA ATAAAGATGG GAGAGCCAGA GGAAGACAAA TATCATCTTC CCCACCCCCG     1500

ACTCTGAGCG AATGAAAGGA GCAGTCGATG ATTAACCCCT AGGCTTTACT CTCACACGTC     1560

AAACTCAACC TCAAGTTGAC AACACTCAAG CTTTGGAGAA GTAAGGGGAC CGACCAGTTT     1620

AAGGCCTCCT GCTTGACATT CAGAGTCAAA CTCCCTGGCG CTGCTCAGTT TTAATTCCTG     1680

GGTCATTTAT CGCCTATTTC TGTTTTCTGA ACCTTAAATT TGGACTCAAT AATATGATGC     1740

AAATCTCTGC TGTGACACTC CCCCCCCCCC CCCACTGGTG TATCAACTGC CCGATTTCTC     1800

AAGATCGACC AAAGAGGTTT TTTCCTTGGT TTGGTCAAC CCTGAGCAGA CCTTAAAGAT     1860

CGGCCAGAGG GAGCAAAGCC CTTTTGACCA TCGCTCCCAA TGCCAGCCTA GAAGTCGGTC     1920

GTCTCTAGTT TACTCAACTA CCCCGAGTTG AGAGCTTGAC CAGGCTTTCC AACAGTTACC     1980

TGTCTTCCCC CGAGGTATTC CTCTATCTAA AGTTGCCCTG TGAATTTTAG TGATCCTGCC     2040

TCATAAATCC AACCAATAAT AATAGAGGGA GGATTTTAAA AATAATTAT CTCATTTCTG      2100

TTAGGTTTAG ACACCACGCA GGAGATAAAT ATTCTCATTA AGCTGATTTC ATCCCCAGAG     2160

TACTGAGCCC CCTCATAAGT GATAATGATC TAGGGAGTGG GAGAGCGAAG ACAAGAACGG     2220

AGAAAGAACA GAAAAGAGCA GGAGACAGAA AGATGGTGAA GGGTGACCCT TAGGCCTGCG     2280

AGGGGATTTA AAAACATCTA CGGGCTTAAG GAACAACAAA TCAATTTACA CGGTTCTGGA     2340

AGAGCCCAGA GGGCCTTTAA TTAATCCCTT CAAAAGAAGG AAGTCGGCCT GGGATGTGCC     2400

TCCTGCCTGC TCCATTAGCT CCCTTTTCGC AAGGGTCCAG ACACCGTTGG AGGTGGGCGC     2460

TGCGCGCAAG CTGGTGGGGG AGGATGACGC GAGCTGGCGT GGGCGGAAGA GACGCACTTA     2520

AACTGCTTTT CCATAGAAGG GCTGGATTTT CATTATTCCT CTCTTTAAAA AGTAATGCCC     2580

TCTTCGTCCG TGCTCCCTCC TTCTCCTTTC CATTTTATTT TGCACAATTA GTTGAGCCGG     2640

CCGCTGGCTC TAGACTGGAA CCACTCTTTT CGCCAGGCCC CTCCCCTCTT GGCTCCGCCC     2700

AAGTGAAGCT GGGGCGGGGA CTAGGAGGGC GCGTCCTTAT GGCTCCCTAG TCTCAGCCAA     2760

TCAAAAGCTG TGGCGCTCCC AGGTAGGCGT GTTCTAGGAG CGACGCCTTG CCCAAGCTGA     2820

GCGCTATTGG AGGCGGTGTT TACGCCCAGG ACCCGGGCCC CGCTCCTCAG TCCCGCCCCG     2880

CCGAGCCGCC CCGGAATGAC GTCCTCGAAA GTTCTCATTT TGGCCCCCCA CCTCCCCTCC     2940

CTTGCGTCCC CCAGCTAAAG AGAGGCAGGG AGGGGTGCAA ATATTTTATT              2990
```

(2) INFORMATION FOR SEQ ID NO:20:

(i) SEQUENCE CHARACTERISTICS:
        (A) LENGTH: 1319 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

| | | | | | |
|---|---|---|---|---|---|
| GAATTCTCAA | AATTGTCAAA | GGGTTTTCCT | TCTCCAGCCC | GCAGTTCAAC | CCTGTCGGGA | 60
| ACGTAAAGAT | CAGCCAGAGA | TGGAAGAGAT | TTAGAGAGTA | AAGGAAGCCA | CCCTTCAACT | 120
| CCTAAACTCT | AGATAGACAT | CCCACCACCA | CTGTCCAGGA | GCTGGTACAT | CTCCATCTCC | 180
| CGTAGCAACT | CTAGAATTGG | GAGTAGGCGC | CAGAGTTTTG | GAGAGGGTTT | TCAAAAGCTT | 240
| ACAGTTCCCA | GGGTGTACCT | AGATGCTTCT | GTATCTAAAG | TTTCCGCCTG | AATTTTGATG | 300
| ATTCTACCCC | CATGTAAACC | CAAAGGAAAT | AACAACAATA | ATCAAAGGGA | GAAAAGTTAA | 360
| GGGAAAAAAC | TCCCTCACTG | TTCTCAGGTA | TAAACATCAT | CTGACAGATA | AATATTCCTA | 420
| TTAAACGGAT | TCAGTTTTCA | GCGAATTGAG | TAACCCATAA | ATGATAATGA | ACGCGGTGGG | 480
| AAGCGACGGG | CGGGGGGGAA | CTCGGGAATG | AAAAAAAAAA | TAAAGTGGAG | GAGAAAGAAC | 540
| AGAAAAGGAA | GCAGGAGGT | GGAAAGATGG | AAGAGGACGA | TCCTTTGGCC | TACAAGGGGA | 600
| TTAAGGACAT | CTATAAGGCT | TAAGGAGCAA | CAAATTAATT | TACACAATTC | TGGGAGAGCC | 660
| CAGATGGCCT | TTAATTAATC | CCTTCAAAAG | AAGGAGCCAG | GCCAGGGCTG | CGCCGGCTGC | 720
| CTGCTCCATT | AGCTCCATTT | TACAAGGGAC | CAGACTTGGT | TCGAGGTGAG | GCGCCCTCCA | 780
| GAGCTGGTGG | GGGAAGGGGA | TAGGATGACG | CGAGCGGGCT | AGTGGGAAG | CAAGGGAAGA | 840
| ATATGAACTG | CTTTTCCATA | AAAGGGCTGA | GTTTTCATTA | TTCCTCTCTT | TAAAAAGTAA | 900
| TACCCTCTTC | GTCTCTGCTT | CCCCCTCCCC | TTTCTCATTT | TATTTAGCAC | AATTAATTGA | 960
| GGCGGCCACT | GGCCCCAGCG | CGGAACCGCA | CCACTCACCA | GCTCCCGCCC | CTCCTGGCCC | 1020
| CGCCCACAGG | AGAAAGAAGT | AGGGAGCGGG | AGGGGACTAG | GCGGGCGCGG | CCCTACGCCT | 1080
| GGCCCGCCTC | AGCCAATCAG | AGGGTGCGGC | GCCCCCGAGT | GGGCGAGCCC | CAGGGGCGAC | 1140
| GCAAGGATCG | AGGCGGCGAG | CTATTGGACA | CGGTGGTTAC | GCCCCCGGCC | TGCGCCCGGC | 1200
| TCGCCGGCCC | CCGCAGCCTC | GGAGTGACGT | CCCTCAAAGT | TCTCATTTTG | GTCCCCCACT | 1260
| TCCCCCTCCC | TTTCGTCCCC | CAGCTAAAGA | GGGGTAGGGA | GTGATGCAAA | TGTTTTATT | 1319

(2) INFORMATION FOR SEQ ID NO:21:

(i) SEQUENCE CHARACTERISTICS:
(A) LENGTH: 1240 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

| | | | | | |
|---|---|---|---|---|---|
| TGTGACACTC | CCCCCCCCCC | CCCACTGGTG | TATCAACTGC | CCGATTTCTC | AAGATCGACC | 60
| AAAGAGGTTT | TTTCCTTGGT | TTTGGTCAAC | CCTGAGCAGA | CCTTAAAGAT | CGGCCAGAGG | 120
| GAGCAAAGCC | CTTTTGACCA | TCGCTCCCAA | TGCCAGCCTA | GAAGTCGGTC | GTCTCTAGTT | 180
| TACTCAACTA | CCCCGAGTTG | AGAGCTTGAC | CAGGCTTTCC | AACAGTTACC | TGTCTTCCCC | 240
| CGAGGTATTC | CTCTATCTAA | AGTTGCCCTG | TGAATTTTAG | TGATCCTGCC | TCATAAATCC | 300
| AACCAATAAT | AATAGAGGGA | GGATTTTAAA | AAATAATTAT | CTCATTTCTG | TTAGGTTTAG | 360
| ACACCACGCA | GGAGATAAAT | ATTCTCATTA | AGCTGATTTC | ATCCCAGAG | TACTGAGCCC | 420
| CCTCATAAGT | GATAATGATC | TAGGGAGTGG | GAGAGCGAAG | ACAAGAACGG | AGAAAGAACA | 480
| GAAAAGAGCA | GGAGACAGAA | AGATGGTGAA | GGGTGACCCT | TAGGCCTGCG | AGGGGATTTA | 540

-continued

| | | | | | |
|---|---|---|---|---|---|
| AAAACATCTA | CGGGCTTAAG | GAACAACAAA | TCAATTTACA | CGGTTCTGGA | AGAGCCCAGA | 600 |
| GGGCCTTTAA | TTAATCCCTT | CAAAAGAAGG | AAGTCGGCCT | GGGATGTGCC | TCCTGCCTGC | 660 |
| TCCATTAGCT | CCCTTTTCGC | AAGGGTCCAG | ACACCGTTGG | AGGTGGGCGC | TGCGCGCAAG | 720 |
| CTGGTGGGGG | AGGATGACGC | GAGCTGGCGT | GGGCGGAAGA | GACGCACTTA | AACTGCTTTT | 780 |
| CCATAGAAGG | GCTGGATTTT | CATTATTCCT | CTCTTTAAAA | AGTAATGCCC | TCTTCGTCCG | 840 |
| TGCTCCCTCC | TTCTCCTTTC | CATTTTATTT | TGCACAATTA | GTTGAGCCGG | CCGCTGGCTC | 900 |
| TAGACTGGAA | CCACTCTTTT | CGCCAGGCCC | CTCCCCTCTT | GGCTCCGCCC | AAGTGAAGCT | 960 |
| GGGGCGGGGA | CTAGGAGGGC | GCGTCCTTAT | GGCTCCCTAG | TCTCAGCCAA | TCAAAAGCTG | 1020 |
| TGGCGCTCCC | AGGTAGGCGT | GTTCTAGGAG | CGACGCCTTG | CCCAAGCTGA | GCGCTATTGG | 1080 |
| AGGCGGTGTT | TACGCCCAGG | ACCCGGGCCC | CGCTCCTCAG | TCCCGCCCCG | CCGAGCCGCC | 1140 |
| CCGGAATGAC | GTCCTCGAAA | GTTCTCATTT | TGGCCCCCCA | CCTCCCCTCC | CTTGCGTCCC | 1200 |
| CCAGCTAAAG | AGAGGCAGGG | AGGGGTGCAA | ATATTTTATT | | | 1240 |